United States Patent
Katayama

(10) Patent No.: US 8,419,621 B2
(45) Date of Patent: Apr. 16, 2013

(54) CAPSULE MEDICAL SYSTEM AND METHOD FOR TREATING DESIRED REGION INSIDE SUBJECT

(75) Inventor: Miho Katayama, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 1048 days.

(21) Appl. No.: 12/418,108

(22) Filed: Apr. 3, 2009

(65) Prior Publication Data

US 2009/0253954 A1 Oct. 8, 2009

(30) Foreign Application Priority Data

Apr. 3, 2008 (JP) ................................. 2008-097308

(51) Int. Cl.
*A61B 1/00* (2006.01)
*A61B 1/04* (2006.01)

(52) U.S. Cl.
USPC ........................... 600/118; 600/106; 600/117

(58) Field of Classification Search .................. 600/106, 600/118
See application file for complete search history.

(56) References Cited

U.S. PATENT DOCUMENTS

| | | | | |
|---|---|---|---|---|
| 6,240,312 B1* | 5/2001 | Alfano et al. | .................. | 600/476 |
| 7,857,767 B2* | 12/2010 | Ferren et al. | .................. | 600/481 |
| 2004/0210343 A1* | 10/2004 | Kim et al. | ...................... | 700/245 |
| 2006/0030754 A1* | 2/2006 | Iddan | ............................. | 600/153 |
| 2006/0167339 A1* | 7/2006 | Gilad et al. | .................... | 600/101 |
| 2006/0224063 A1* | 10/2006 | Segawa et al. | ................. | 600/424 |
| 2007/0173691 A1* | 7/2007 | Yokoi et al. | .................... | 600/118 |
| 2007/0255098 A1* | 11/2007 | Wang et al. | .................... | 600/109 |
| 2008/0039692 A1* | 2/2008 | Hirakawa | ....................... | 600/160 |
| 2008/0294143 A1* | 11/2008 | Tanaka et al. | .................. | 604/506 |
| 2008/0297291 A1* | 12/2008 | Kawano et al. | ................ | 335/285 |
| 2009/0143697 A1* | 6/2009 | Tanaka | ........................... | 600/565 |
| 2009/0227837 A1* | 9/2009 | Shimizu et al. | ............... | 600/109 |
| 2009/0281387 A1* | 11/2009 | Takizawa et al. | .............. | 600/117 |
| 2009/0312787 A1* | 12/2009 | Chiba et al. | .................... | 606/194 |
| 2010/0049033 A1* | 2/2010 | Kawano et al. | ................ | 600/424 |

(Continued)

FOREIGN PATENT DOCUMENTS

| | | | |
|---|---|---|---|
| JP | 2004-041709 | 2/2004 | |
| JP | 2005-334331 | 12/2005 | |
| JP | 2006-218239 | 8/2006 | |
| WO | WO-2008/149674 | * 11/2008 | .................... 382/107 |

OTHER PUBLICATIONS

Japanese Office Action dated Oct. 30, 2012 received in corresponding Japanese Application No. 2008-097308 together with an English Language Translation.

*Primary Examiner* — John P Leubecker
*Assistant Examiner* — Arnaldo Torres Diaz
(74) *Attorney, Agent, or Firm* — Scully Scott Murphy & Presser, PC

(57) ABSTRACT

A capsule medical system includes a capsule medical apparatus, a selecting unit, and a control unit. The capsule medical apparatus is introduced inside a subject and includes an imaging unit for taking an in-vivo image of the subject, a treating unit for treating a living tissue in the subject, and a driving unit for contributing to movement of the capsule medical apparatus. The selecting unit selects a treatment target of the treating unit from the in-vivo image. The control unit determines a relative distance between the treatment target and the treating unit, and moves the capsule medical apparatus in an imaging direction of the imaging unit by a distance corresponding to the relative distance using the driving unit.

11 Claims, 11 Drawing Sheets

U.S. PATENT DOCUMENTS

2010/0061597 A1* 3/2010 Kanda et al. .................. 382/107
2010/0179381 A1* 7/2010 Kawano et al. ............... 600/104
2012/0041291 A1* 2/2012 Ferren et al. .................. 600/365

* cited by examiner

CAPSULE MEDICAL SYSTEM AND METHOD FOR TREATING DESIRED REGION INSIDE SUBJECT

CROSS-REFERENCE TO RELATED APPLICATIONS

This application is based upon and claims the benefit of priority from Japanese Patent Application No. 2008-097308, filed on Apr. 3, 2008, the entire contents of which are incorporated herein by reference.

BACKGROUND OF THE INVENTION

1. Field of the Invention

The present invention relates to a capsule medical system and a method for treating a desired region inside a subject which give medical treatment to a living tissue of an internal body part with a capsule medical apparatus introduced inside a subject.

2. Description of the Related Art

Conventionally, in a field of endoscope, a capsule endoscope that is introduced inside an organ of a subject and that takes images of the inside of the organ (hereinafter, referred to as "in-vivo image" also) has been available. A capsule endoscope has an imaging function and a wireless communication function thereinside, and after orally introduced inside a subject such as a patient body, the capsule endoscope sequentially images in-vivo images of the subject while traveling inside a digestive canal by peristaltic movement and the like, and sequentially transmits the in-vivo images to a receiver apparatus placed outside the subject by wireless communication at each imaging. This capsule endoscope inside the subject is discharged out of the subject together with excrements or the like.

Among capsule medical systems that gives treatment to a subject using a capsule medical apparatus such as the capsule endoscope, there is a one that introduces a capsule medical apparatus carrying medicine inside a casing thereof inside a subject, and that gives the medicine to an affected part with this capsule medical apparatus inside the subject (Japanese Patent Laid-Open Publication No. 2005-334331). In the system described in this patent document 1, the position of an affected part inside the subject is identified using a medical diagnostic equipment such as an X-ray computerized topology (CT) and a magnetic resonance imaging (MRI), and the capsule medical apparatus is caused to release the medicine when the capsule medical apparatus reaches the identified position of the affected part.

SUMMARY OF THE INVENTION

A capsule medical system according to one aspect of the present invention includes a capsule medical apparatus that is introduced inside a subject, and includes an imaging unit that takes an in-vivo image of the subject, a treating unit that performs treatment on a living tissue inside the subject, and a driving unit that contributes to movement of the capsule medical apparatus; a selecting unit that selects a treatment target of the treating unit from the in-vivo image; and a control unit that determines a relative distance between the treatment target and the treating unit, and that moves the capsule medical apparatus in an imaging direction of the imaging unit by a distance corresponding to the relative distance using the driving unit.

A method according to another aspect of the present invention is for treating a desired region inside a subject with a capsule medical apparatus. The method includes selecting a treatment target inside the subject; calculating relative positions of the treatment target and the capsule medical apparatus; moving the capsule medical apparatus based on the calculated relative positions; fixing positions of the treatment target and the capsule medical apparatus; and treating the treatment target with the capsule medical apparatus.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a capsule medical system according to the present invention are explained in detail below with reference to the accompanying drawings. In a following example, a capsule medical system that performs excision of a lesion tissue in an internal body part as one example of treatment to be performed on a living tissue inside a subject is explained; however, the present invention is not limited by this embodiment.

Figure 1:
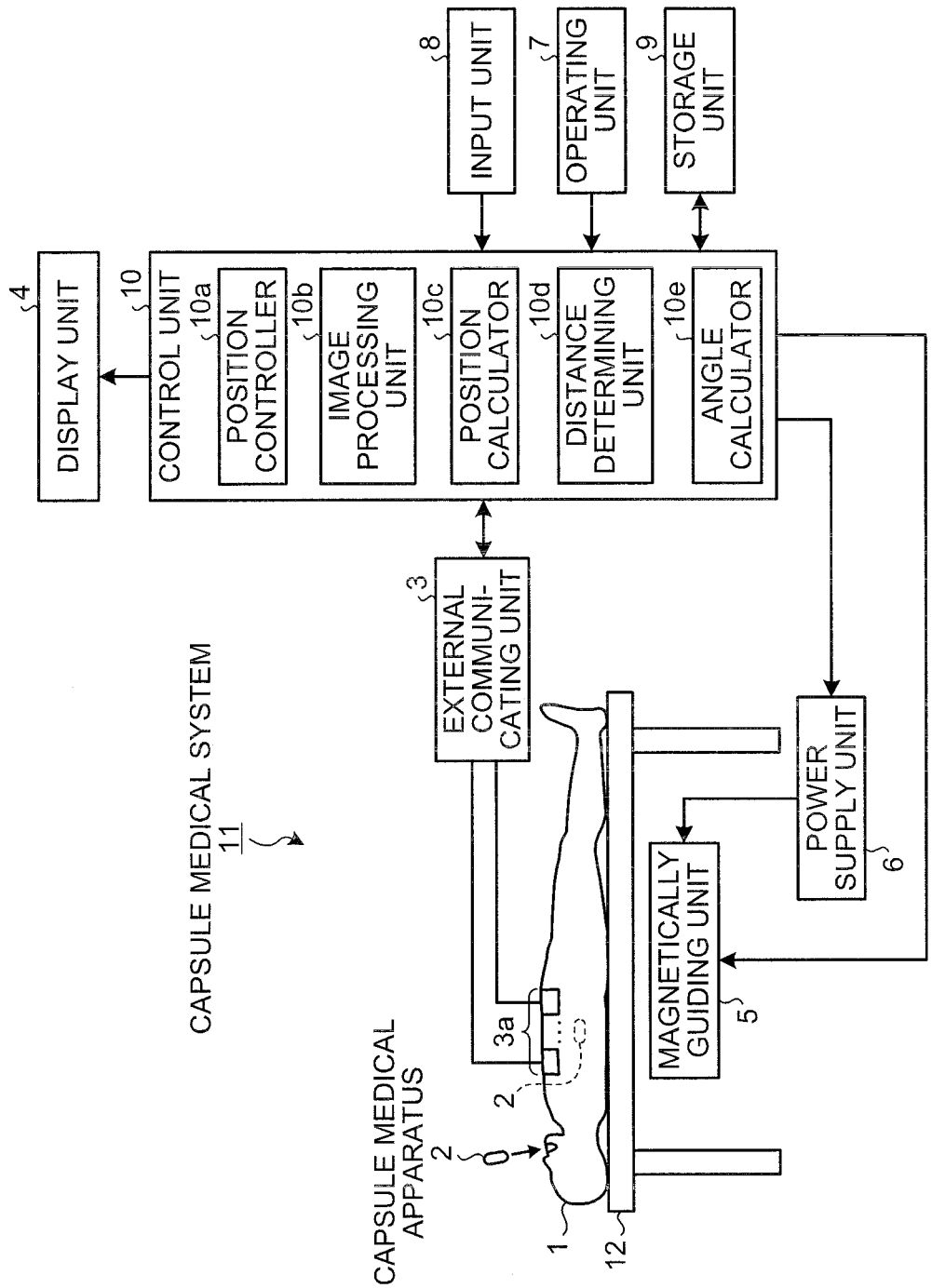
FIG. 1 is a block diagram schematically showing a configuration example of a capsule medical system according to a first embodiment of the present invention.

FIG. 1 is a block diagram schematically showing a configuration example of a capsule medical system according to a first embodiment of the present invention. As shown in FIG. 1, a capsule medical system 11 according to the first embodiment includes a capsule medical apparatus 2 that is introduced inside a subject 1 such as a patient body, an external communicating unit 3 that performs wireless communication with the capsule medical apparatus 2 inside the subject 1 through a plurality of antennas 3a that are arranged on a body surface of the subject 1, and a display unit 4 that displays various kinds of information such as an in-vivo image of the subject 1 that is taken by the capsule medical apparatus 2. In addition, the capsule medical system 11 includes a magnetically guiding unit 5 that guides the capsule medical apparatus 2 inside the subject 1 by magnetic force, a power supply unit 6 that supplies electric power to the magnetically guiding unit 5, and an operating unit 7 that operates the guidance of the capsule medical apparatus 2 by this magnetically guiding unit 5. Furthermore, the capsule medical system 11 includes an input unit 8 that inputs various kinds of information, a storage unit 9 that stores various kinds of information such as an in-vivo image of the subject 1, and a control unit 10 that controls respective components of the capsule medical system 11.

The capsule medical apparatus 2 is a medical apparatus in a capsule shape that is formed in a size small enough to be introduced inside the subject 1, and has an imaging function for taking in-vivo images of the subject 1 and a wireless communication function for performing wireless communication with the external communicating unit 3 placed outside. Specifically, the capsule medical apparatus 2 is introduced inside the subject 1 by oral intake or the like, and is moved by an effect of an external magnetic field caused by the magnetically guiding unit 5 or peristaltic movement and the like to travel inside a digestive canal of the subject 1. The capsule medical apparatus 2 sequentially takes in-vivo images of the subject 1 while traveling inside a digestive canal of the subject 1, and transmits information such as the obtained in-vivo image to an external device outside the subject 1 by wireless communication at each imaging.

Moreover, the capsule medical apparatus 2 has a tissue obtaining function for obtaining a living tissue of an internal body part inside the subject 1. Specifically, the capsule medical apparatus 2 travels inside a digestive canal of the subject 1 by an effect of an external magnetic field caused by the magnetically guiding unit 5 or peristaltic movement and the like to reach a desirable internal body part (for example, an internal body part at which a treatment target such as a lesion tissue is present) inside the subject 1. The capsule medical apparatus 2 is moved to a position corresponding to a treatment target such as a lesion tissue in this internal body part by the effect of a magnetic field that is formed by the magnetically guiding unit 5 based on a control of the external control unit 10, and performs highly accurate positioning of a treating unit (treating unit 23 described later) that gives treatment to a living tissue so as to match with the position of this treatment target. In this state, the capsule medical apparatus 2 obtains the living tissue of the treatment target with this treating unit based on an instruction from an external device (specifically, a control signal from the external control unit 10). Thereafter, the capsule medical apparatus 2 travels inside the digestive canal of the subject 1 with this obtained living tissue held inside a capsule casing, and is discharged out of the subject 1 in the end.

The external communicating unit 3 is connected to the antennas 3a that are arranged on the body surface of the subject 1, and performs wireless communication with the capsule medical apparatus 2 inside the subject 1 through either one of the antennas 3a. The external communicating unit 3 receives a radio signal from the capsule medical apparatus 2 through the antennas 3a, and performs a demodulation processing and the like on this received radio signal to extract information such as an image signal included in this radio signal. The external communicating unit 3 transmits the information such as an image signal to the control unit 10. The image signal extracted (demodulated) by the external communicating unit 3 includes an in-vivo image that is taken inside the subject 1 by the capsule medical apparatus 2. On the other hand, the external communicating unit 3 obtains a control signal to control the capsule medical apparatus 2 from the control unit 10, and performs a predetermined demodulation processing and the like on this obtained control signal to generate a radio signal including this control signal. The external communicating unit 3 transmits this generated radio signal to the capsule medical apparatus 2 inside the subject 1 through the antennas 3a.

The antennas 3a are communication antennas that are used for wireless communication between the capsule medical apparatus 2 introduced inside the subject 1 and the external communicating unit 3 outside the subject 1, and are arranged in a dispersed manner on the body surface of the subject 1 into which the capsule medical apparatus 2 is introduced. Among the antennas 3a, at least one antenna picks up a radio signal from the capsule medical apparatus 2 that is positioned inside the subject 1 (for example, in a digestive canal such as an esophagus, a stomach, a small intestine, and a large intestine) and transmits the signal to the external communicating unit 3. Furthermore, the antenna 3a transmits a radio signal from the external communicating unit 3 to the capsule medical apparatus 2 inside the subject 1.

The display unit 4 is implemented by various kinds of displays such as a cathode ray tube (CRT) display and a liquid crystal display, and displays various kinds of information that the control unit 10 instructs to display. Specifically, the display unit 4 displays a group of in-vivo images of the subject 1 that are imaged by the capsule medical apparatus 2, patient information of the subject 1 and examination information that are input by the input unit 8, information on a current position of the capsule medical apparatus 2 inside the subject 1, and the like.

The magnetically guiding unit 5 is implemented by a plurality of electromagnets and the like, and forms an external three-dimensional magnetic field such as a rotating magnetic field and a gradient magnetic field by electric power supplied by the power supply unit 6. The magnetically guiding unit 5 applies the formed external magnetic field to the capsule medical apparatus 2 inside the subject 1 that is placed on a bed 12 to guide the capsule medical apparatus 2 inside the subject 1 to a desirable position by the effect of this external magnetic field. Moreover, the magnetically guiding unit 5 fixes the capsule medical apparatus 2 on an internal wall of an organ of the subject 1 by the magnetic force of the external magnetic field.

The power supply unit 6 supplies electric power to form the external magnetic field to be applied to the capsule medical apparatus 2 inside the subject 1, to the magnetically guiding unit 5. Specifically, the power supply unit 6 supplies alternating current to the magnetically guiding unit 5 based on a control of the control unit 10, thereby causing to the magnetically guiding unit 5 to form the external three-dimensional magnetic field such as a rotating magnetic field and a gradient magnetic field. In other words, the external magnetic field formed by the magnetically guiding unit 5 described above is controlled by the alternating current supplied by the power supply unit 6 (amount of electric power supplied by the power supply unit 6).

The operating unit 7 is to operate the guidance of the capsule medical apparatus 2 inside the subject 1 by the external magnetic field formed by the magnetically guiding unit 5. Specifically, the operating unit 7 is implemented by an input device such as an input button and a joy stick, and inputs instruction information that instructs the magnetic guidance of the capsule medical apparatus 2 to the control unit 1 based on operation input by a user such as a doctor and a nurse. The instruction information input by the operating unit 7 instructs movement (travel and rotation) of the capsule medical apparatus 2 that is made by movement in a horizontal direction with respect to the long axis of the capsule medical apparatus 2, movement in a vertical direction with respect to the long axis, rotation about the long axis, movement in a slanting direction with respect to the long axis, or combination thereof.

The input unit 8 is implemented by an input device such as a keyboard, a mouse, and a touch panel, and inputs various kinds of information to the control unit 10 based on operation input by a user such as a doctor and a nurse. Moreover, the input unit 8 functions as a selecting unit that selects a desirable treatment target (for example, a living tissue such as a lesion tissue) from among the in-vivo images displayed on the display unit 4. The input unit 8 inputs information on selection of a desirable treatment target that is shown in an in-vivo image to the control unit 10, by input operation made by placing a cursor displayed on the display unit 4 on the desirable treatment target and determining the treatment target. Other than the selection information of a treatment target described above, the information input to the control unit 10 by the input unit 8 includes, for example, instruction information to instruct the control unit 10, patient information of a subject, examination information of a subject, and position coordinate information of a treatment target on a biaxial rectangular coordinate system of the display unit 4.

The patient information of a subject is information to identify a subject, and includes, for example, patient name, patient identification (ID), date of birth, sex, age, and the like of a subject. The examination information of a subject is information to identify a biopsy performed using a living tissue obtained from an internal body part by the capsule medical apparatus 2 introduced inside the subject 1, and includes, for example, an examination ID, a date of examination, and the like. The biaxial rectangular coordinate system set in the display unit 4 is a coordinate system that is defined by, for example, axes in a vertical direction and in a horizontal direction of a display screen.

The storage unit 9 is implemented by various kinds of storage media that rewritably store information, such as a random access memory (RAM), an electrically erasable and programmable read only memory (EEPROM), a flash memory, and a hard disk. The storage unit 9 stores various kinds of information for which the control unit 10 gives a storage instruction, and sends, to the control unit 10, information for which the control unit 10 gives a read instruction. The storage unit 9 stores a group of in-vivo images of the subject 1, the patient information and the examination information of the subject 1, current position information of the capsule medical apparatus 2 inside the subject 1, the position coordinate information of a treatment target that is selected from the in-vivo images displayed on the display unit 4, and the like.

The control unit 10 controls the respective components (the capsule medical apparatus 2, the external communicating unit 3, the display unit 4, the magnetically guiding unit 5, the power supply unit 6, the operating unit 7, the input unit 8, and the storage unit 9) of the capsule medical system 11, and controls input and output of a signal among the respective components. Specifically, the control unit 10 controls operation of the external communicating unit 3, the display unit 4, and the storage unit 9 based on instruction information input by the input unit 8. Moreover, the control unit 10 controls operation of the magnetically guiding unit 5 and an amount of electric power supplied to the magnetically guiding unit 5 by the power supply unit 6, and controls a direction and an intensity of the magnetic field of the magnetically guiding unit 5 by controlling the amount of electric power supplied by the power supply unit 6 based on instruction information input by the operating unit 7 or the input unit 8. The control unit 10 controls the magnetic guidance of the capsule medical apparatus 2 inside the subject 1 by controlling the magnetically guiding unit 5. Meanwhile, the control unit 10 generates a control signal to instruct a series of obtaining operation to obtain a living tissue of an internal body part, to the capsule medical apparatus 2 inside the subject 1 based on instruction information (specifically, instruction information to instruct a series of the obtaining operation by the capsule medical apparatus 2) input by the input unit 8. The control unit 10 controls the external communicating unit 3 to send the control signal to the capsule medical apparatus 2 inside the subject 1, and controls the capsule medical apparatus 2 inside the subject 1 by the control signal.

Further, the control unit 10 includes a position controller 100a, an image processing unit 10b, a position calculator 10c, a distance determining unit 10d, and an angle calculator 10e. The position control unit 10a controls positioning of the treating unit the capsule medical apparatus 2 inside the subject 1 relative to a treatment target inside the subject 1. The image processing unit 10b generates an in-vivo image of the subject 1. The position calculator 10c calculates a position of the capsule medical apparatus 2 inside the subject 1. The distance determining unit 10d determines a relative distance between a living tissue being a treatment target and the treating unit of the capsule medical apparatus 2. The angle calculator 10e calculates a rotation angle of the capsule medical apparatus 2 relative to a treatment target.

The position control unit 10a controls the operation of the magnetically guiding unit 5 and the amount of electric power supplied by the power supply unit 6, and controls the positioning of the treating unit of the capsule medical apparatus 2 inside the subject 1 relative to a living tissue being a treatment target in an internal body part by controlling the magnetically guiding unit 5 and the power supply unit 6. The position control unit 10a moves the capsule medical apparatus 2 by a distance determined by the distance determining unit 10d, that is, a relative distance between a treatment target and the treating unit of the capsule medical apparatus 2. Thus, the position control unit 10a accurately controls the positioning of the capsule medical apparatus 2 with respect to a treatment target. Furthermore, the position control unit 10a rotates the capsule medical apparatus 2 by a rotation angle calculated by the angle calculator 10e, thereby controlling the positioning of the capsule medical apparatus 2 with respect to a treatment target in a rotation direction accurately.

The image processing unit 10b obtains, from the external communicating unit 3, an image signal that is demodulated from a radio signal from the capsule medical apparatus 2, and generates (reconstructs) image information corresponding to this image information, that is, an in-vivo image of the subject 1, by performing a predetermined image processing on this obtained image signal. A group of in-vivo images generated by the image processing unit 10b are displayed on the display unit 4 and stored in the storage unit 9 as described above.

The position calculator 10c obtains, from the external communicating unit 3, information on a reception electric-field intensity of each antenna (for example, top three reception electric-field intensities of the antennas 3a) when the external communicating unit 3 sequentially receives radio signals from the capsule medical apparatus 2 through the antennas 3a. The position calculator 10c calculates a current position of the capsule medical apparatus 2 inside the subject 1 by a trigonometry or the like based on the obtained reception electric-field intensity and position information of each antenna in the antennas 3a. The control unit 10 associates the current position information calculated by the position calculator 10c and the in-vivo image of the subject 1 imaged by the capsule medical apparatus 2 present at the current position. The in-vivo image of the subject 1 and the current position information of the capsule medical apparatus 2 that are associated by the control unit 10 are displayed on the display unit 4 and stored in the storage unit 9.

The distance determining unit 10d determines a relative distance between a living tissue being a treatment target that is selected by using the input unit 8 from an in-vivo image displayed on the display unit 4 and the treating unit of the capsule medical apparatus 2. In detail, the distance determining unit 10d determines the relative distance between the living tissue being a treatment target and the treating unit of the capsule medical apparatus 2 when the capsule medical apparatus 2 stops at a position (hereinafter, "specific position") inside the subject 1 at which such an in-vivo image that the treatment target is shown at an edge portion of an image can be taken in contact with an internal wall of an organ. By moving the capsule medical apparatus 2 by the relative distance in an imaging direction of the in-vivo image, the position of the treating unit of the capsule medical apparatus 2 and the position of the treatment target can be accurately matched (position in the long axis of the capsule medical apparatus 2).

The angle calculator 10e calculates a rotation angle that is required to match the position of a living tissue being the treatment target that is selected by using the input unit 8 from an in-vivo image displayed on the display unit 4 and the position of the treating unit of the capsule medical apparatus 2 in the rotation direction. Specifically, the angle calculator 10e, in advance, has position coordinate information of the treating unit in the biaxial rectangular coordinate system set in the display unit 4. Furthermore, the angle calculator 10e obtains position coordinate information of the treatment target input by the input unit 8, that is, the position coordinate information of the treatment target in the biaxial rectangular coordinate system of the display unit 4. The angle calculator 10e calculates an angle formed between a direction of the treatment target and a direction of the treating unit in the biaxial rectangular coordinate system of the display unit 4, that is, a rotation angle of the capsule medical apparatus 2 relative to the treatment target, based on the position coordinate information of the treating unit and the treatment target. By rotating the capsule medical apparatus 2 by the rotation angle about the long axis, the position of the treating unit of the capsule medical apparatus 2 and the position of the treatment target in a rotation direction can be accurately matched.

Figure 2:
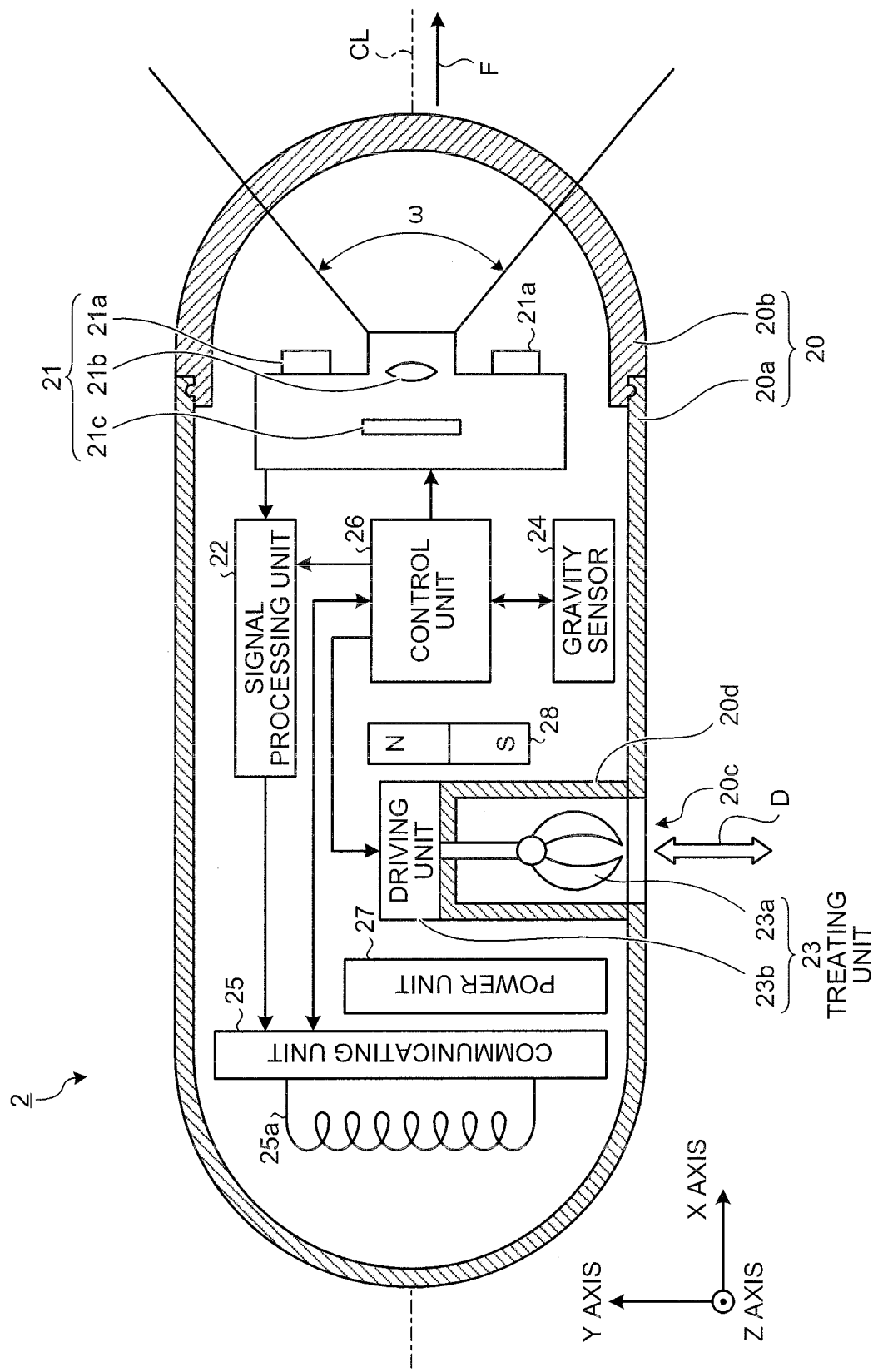
FIG. 2 is a schematic diagram showing a configuration example of a capsule medical apparatus according to the first embodiment of the present invention.

Next, a configuration of the capsule medical apparatus 2 according to the first embodiment of the present invention is explained in detail. FIG. 2 is a schematic diagram showing a configuration example of the capsule medical apparatus according to the first embodiment of the present invention. As shown in FIG. 2, the capsule medical apparatus 2 according to the first embodiment includes a capsule casing 20 that is formed with a tubular casing 20a and a dome-shaped casing 20b, an imaging unit 21 that images an in-vivo image of the subject 1, a signal processing unit 22 that generates an image signal including the in-vivo image that is imaged by the imaging unit 21, a treating unit 23 that gives treatment to a desirable part inside a body, and a gravity sensor 24 that detects an angle between a direction of this treating unit 23 and a gravity direction. Furthermore, the capsule medical apparatus 2 includes a communicating unit 25 that communicates with the external communicating unit 3 (see FIG. 1) by wireless communication, a control unit 26 that controls respective components of the capsule medical apparatus 2, a power unit 27 that is implemented by a battery or the like, and a magnet 28 that acts following the external magnetic field formed by the magnetically guiding unit 5 described above.

The capsule casing 20 is a capsule-shaped casing that is formed small enough to be introduced inside the subject 1, and is formed with the tubular casing 20a having a dome shape on one end and the dome-shaped casing 20b closing the other end (opening end) of the tubular casing 20a. The dome-shaped casing 20b is an optical dome that is transparent to light in a predetermined wavelength range (for example, visible light). On the other hand, the tubular casing 20a is substantially opaque casing, and an opening 20c through which the treating unit 23 is taken in and out is formed at a part of the tubular casing 20a. In the capsule casing 20 formed with the tubular casing 20a and the dome-shaped casing 20b, the imaging unit 21, the signal processing unit 22, the treating unit 23, the gravity sensor 24, the communicating unit 25, the control unit 26, the power unit 27, and the magnet 28 are housed. The treating unit 23 is arranged near the opening 20c of the capsule casing 20. The imaging unit 21 is arranged at a fixed position relative to the treating unit 23 (in detail, an obtaining unit 23a described later). In other words, the relative distance (hereinafter, "inter-parts distance") between the imaging unit 21 and the treating unit 23 is fixed inside the capsule casing 20.

To the capsule medical apparatus 2 that has the capsule casing 20 as an exterior thereof, a triaxial rectangular coordinate system having three axes of X, Y, and Z is set. In this triaxial rectangular coordinate system, an X axis coincides with a center axis CL in a longitudinal direction of the capsule casing 20, and a Y axis and a Z axis are perpendicular to each other and coincide with a direction perpendicular to the center axis CL, that is, the center axis in a direction of diameter of the capsule casing 20.

The imaging unit 21 is to image an in-vivo image of the subject 1, and includes illuminating units 21a such as a light emitting diode (LED), an optical system 21b such as a condenser lens, and a solid-state imaging device 21c such as a charge-coupled device (CCD). The illuminating units 21a illuminate a subject of imaging (specifically, an interior of an organ of the subject 1) through the dome-shaped casing 20b. The optical system 21b condenses reflected light from the subject illuminated by the illuminating units 21a, to form an optical image of the subject on a photosensitive surface of the solid-state imaging device 21c. The solid-state imaging device 21c receives the reflected light from the subject through the photosensitive surface, and images the optical image of the subjected formed by the optical system 21b. The imaging unit 21 having such a configuration has an imaging direction F that is same as the direction of the center axis CL described above (that is, the direction of X axis, which is the longitudinal direction of the capsule casing 20), and an angle of view ω, and images an optical image of the subject in an imaging field of view that is defined by the imaging direction F and the angel of view ω, that is, an in-vivo image of the subject 1.

Figure 3:
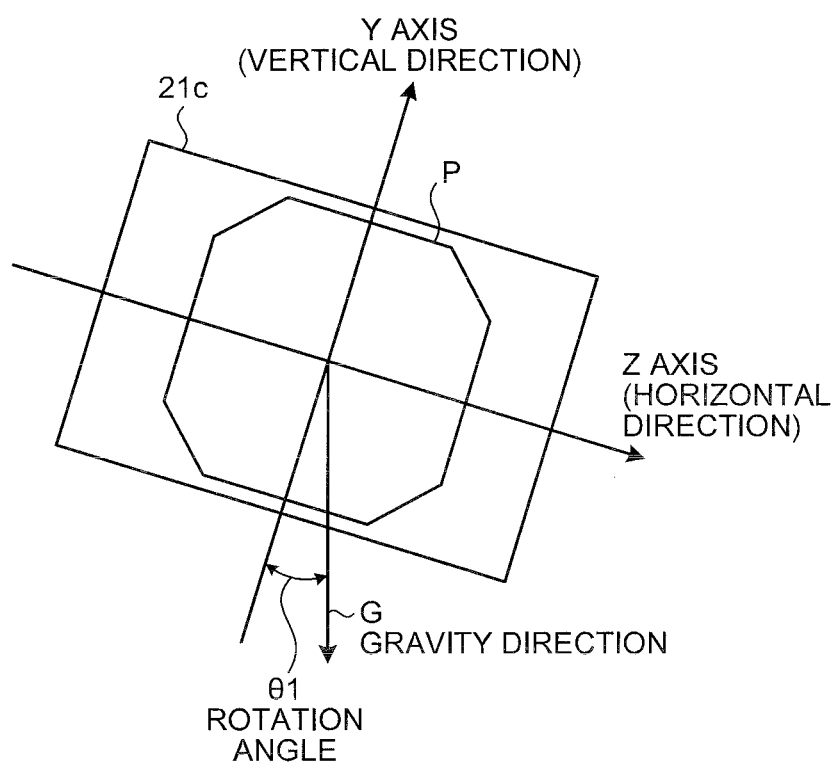
FIG. 3 is a schematic diagram for explaining a biaxial rectangular coordinate system set in an in-vivo image.

As described above, in the capsule medical apparatus 2 in which the triaxial rectangular coordinate system of XYZ is set, the photosensitive surface of the solid-state imaging device 21c is a flat plane of a biaxial rectangular coordinate system formed by the Y axis and the Z axis as shown in FIG. 3. A vertical direction of this photosensitive surface coincides with the direction of the Y axis and a horizontal direction of this photosensitive surface coincides with the direction of the Z direction. In this case, a vertical direction of an in-vivo image P of the subject 1 that is imaged by the solid-state imaging device 21c coincides with the direction of the Y axis and a horizontal direction of the in-vivo image P coincides with the direction of the Z axis.

Furthermore, the solid-state imaging device 21c of the imaging unit 21 that is arranged inside the capsule casing 20 rotates along the rotation of the capsule medical apparatus 2 about the center axis CL, and as a result, a rotation angle θ1 between the vertical direction (direction of the Y axis) of the solid-state imaging device 21c and a gravity direction G is formed. The rotation angle θ1 between the vertical direction of the solid-state imaging device 21c and the gravity direction G is, for example, an angle whose forward direction is a clockwise direction toward the direction of the X axis, and is detected by the gravity sensor 24 described later. The rotation angle θ1 is equivalent to a rotation angle formed between an in-and-out direction (one example of a treating unit direction) of the treating unit 23 described later and the gravity direction G.

The signal processing unit 22 obtains a signal subjected to a photoelectric conversion by the solid-state imaging device 21c of the imaging unit 21, and performs a predetermined process on the obtained signal to generate an image signal including an in-vivo image of the subject 1. The signal processing unit 22 sequentially transmits a generated image signal to the communicating unit 25 at each generation of an image signal.

The treating unit 23 functions as a treating unit that performs treatment on a treatment target such as a lesion tissue, and performs obtaining of a desirable tissue such as a lesion tissue from an internal body part, as one example of the treatment performed on a living tissue. Specifically, the treating unit 23 has a forcipate obtaining unit 23a to excise and obtain a living tissue from an internal body part of the subject 1, and a driving unit 23b that causes the obtaining unit 23a to perform a series of obtaining operation to obtain a living tissue.

The obtaining unit 23a has a forcipate form as shown in FIG. 2, and performs a series of the obtaining operation to obtain a living tissue being a treatment target from an internal body part by the action of the driving unit 23b. Specifically, the obtaining unit 23a is housed in a housing unit 20d that is provided inside the capsule casing 20, and is caused to project out of the capsule casing 20 from the opening 20c by the action of the driving unit 23b. The obtaining unit 23a projects toward the living tissue being the treatment target, and then, opens and closes a forcipate end portion by the action of the driving unit 23b to excise and obtain the living tissue from the internal body part. After obtaining this living tissue, the obtaining unit 23a is moved back inside the capsule casing 20 by the action of the driving unit 23b, and is housed inside the housing unit 20d finally. As described, the obtaining unit 23a finishes one cycle of a series of the obtaining operation. The living tissue obtained by the obtaining unit 23a is kept inside the capsule casing 20 being held at the forcipate end portion of the obtaining unit 23a.

An in-and-out direction D of the obtaining unit 23a is one example of the treating unit direction in the present embodiment. The capsule medical apparatus 2 achieves accurate positioning of the obtaining unit 23a with respect to a treatment target in the direction of the center axis CL and the rotation direction, by positioning the treatment target in the in-and-out direction D when the capsule medical apparatus 2 reaches near the treatment target such as a lesion tissue.

The driving unit 23b is implemented by an actuator or the like, and causes the obtaining unit 23a to perform a series of the obtaining operation based on a control of the control unit 26. The driving unit 23b causes the obtaining unit 23a to execute one cycle of a series of the obtaining operation each time a control signal from the control unit 26 is received, that is, at each control by the control unit 26. The housing unit 20d is a tubular member that houses the obtaining unit 23a described above. The housing unit 20d communicates with the outside of the capsule casing 20 through the opening 20c, and separates a housing area of the obtaining unit 23a from an interior of the capsule casing 20 in which electronic parts such as the control unit 26 and the power unit 27 are housed.

The gravity sensor 24 detects an angle between a direction of the treating unit 23 (that is, the in-and-out direction D of the obtaining unit 23a) and the gravity direction G, formed when the capsule medical apparatus 2 rotates about the center axis CL in the longitudinal direction. The in-and-out direction D of the obtaining unit 23a shown in FIG. 2 is a fixed direction in the capsule medical apparatus 2, and for example, coincides with the direction of the Y axis in the triaxial rectangular coordinate system described above. In this case, the in-and-out direction D coincides with a vertical direction (direction of the Y axis) of the solid-state imaging device 21c shown in FIG. 3. In other words, the gravity sensor 24 detects the rotation angle θ1 (see FIG. 3) described above as the angle formed between the in-and-out direction D of the obtaining unit 23a and the gravity direction G. The gravity sensor 24 transmits a result of detection of the rotation angle θ1 to the control unit 26.

The rotation angle θ1 is notified to the external control unit 10 (see FIG. 1) through the external communicating unit 3 and the like. The control unit 10 obtains an angle (the rotation angle θ1) detected by the gravity sensor 24 through the external communicating unit 3 and the like, corrects a rotation gap of the in-vivo image P based on the obtained angle, to match an axis direction of the biaxial rectangular coordinate system of the display unit 4 (for example, a vertical direction of the display unit) and a direction of the in-vivo image P corresponding to the in-and-out direction D of the obtaining unit 23a. The control unit 10 causes the display unit 4 to display the in-vivo image P in a state where that the axis direction of the biaxial rectangular coordinate system of the display unit 4 and the direction of the in-vivo image P corresponding to the in-and-out direction D of the obtaining unit 23a are matched. Thus, the biaxial rectangular coordinate system of the display unit 4 coincides with the biaxial rectangular coordinate system of the in-vivo image P formed by the Y axis and the Z axis described above. As a result, a user such as a doctor and a nurse can easily understand the Y axis direction and the Z axis direction of the capsule medical apparatus 2 inside the subject 1 by each direction of upward, downward, rightward, and leftward of the in-vivo image P displayed on the display unit 4, and can easily operate the magnetic guidance of the capsule medical apparatus 2 inside the subject 1 by referring to the in-vivo image P.

The communicating unit 25 has a coiled antenna 25a, and performs wireless communication with the external communicating unit 3 (see FIG. 1) outside the subject 1 using this antenna 25a. Specifically, the communicating unit 25 transmits an in-vivo image of the subject 1 and detection angle information given by the gravity sensor 24 to an external device by wireless communication based on a control of the control unit 26. The communicating unit 25 obtains the image signal that is generated by the signal processing unit 22 and the rotation angle $\theta 1$ that is detected by the gravity sensor 24 at the time of imaging the in-vivo image corresponding to this image signal. The communicating unit 25 generates a radio signal including the image signal and the detection angle information (the rotation angle $\theta 1$) of the gravity sensor 24, and transmits the generated radio signal to an external device. The radio signal including the image signal and the detection angle information is received by the external communicating unit 3 through the antennas 3a described above.

The communicating unit 25 receives a radio signal from the external communicating unit 3 through the antenna 25a based on a control of the control unit 26, and performs a predetermined demodulation processing or the like thereon to extract a control signal included in this radio signal. The control signal demodulated by the communicating unit 25 is the control signal that is generated by the external control unit 10, and is the control signal to instruct the capsule medical apparatus 2 to perform a series of the obtaining operation to obtain a living tissue of an internal body part. The communicating unit 25 transmits the control signal from the external control unit 10 to the control unit 26.

The control unit 26 controls the respective components (the imaging unit 21, the signal processing unit 22, the treating unit 23, the gravity sensor 24, and the communicating unit 25) of the capsule medical apparatus 2, and controls input and output of a signal among the respective components. Specifically, the control unit 26 controls the imaging unit 21 to take an image of a subject (that is, an in-vivo image) illuminated by the illuminating units 21a with the solid-state imaging device 21c, and causes the gravity sensor 24 to detect the rotation angle $\theta 1$ at the time of causing the imaging unit 21 to take the in-vivo image. Furthermore, the control unit 26 controls the signal processing unit 22 and the communicating unit 25 to transmit the radio signal including the in-vivo image and the detection angle information provided by the gravity sensor 24 to an external device. On the other hand, the control unit 26 obtains the control signal from the external control unit 10, and controls a series of the obtaining operation performed by the treating unit 23 based on the obtained control signal. In this case, the control unit 26 controls the driving unit 23d of the treating unit 23 based on the control signal, and controls the operation of the obtaining unit 23a, that is, a series of the obtaining operation, by controlling the driving unit 23b.

The power unit 27 is implemented by a switching circuit, a button cell, or the like, and supplies power to the imaging unit 21, the signal processing unit 22, the treating unit 23, the gravity sensor 24, the communicating unit 25, and the control unit 26.

The magnet 28 is implemented by a permanent magnet, an electromagnet, or a magnetic substance, and is fixed inside the tubular casing 20a in such a manner that the magnet 28 is polarized in a direction perpendicular to the center axis CL in the longitudinal direction of the capsule casing 20 (that is, a direction of diameter of the capsule casing 20). The magnet 28 acts according to the external magnetic field formed by the magnetically guiding unit 5 (see FIG. 1) described above. Thus, the magnet 28 moves the capsule medical apparatus 2 in the axis directions (the X axis direction, the Y axis direction, and the Z axis direction) in the triaxial rectangular coordinate system, and rotates the capsule medical apparatus 2 about the axes (about the X axis, the Y axis, and the Z axis) of the triaxial rectangular coordinate system. By the effect of the magnet 28, the capsule medical apparatus 2 is magnetically guided to a desirable position in an internal body part of the subject 1, arranged in a desirable orientation, or fixed on an internal wall of an organ.

The capsule medical apparatus 2 having such a configuration is introduced inside the subject 1 in the capsule medical system 11 shown in FIG. 1. Thereafter, the capsule medical apparatus 2 sequentially images the in-vivo image P of the subject 1 while traveling inside a digestive canal of the subject 1 by peristaltic movement or the effect of the external magnetic field formed by the magnetically guiding unit 5, and sequentially transmits the in-vivo image P and an amount of rotation gap (that is, the rotation angle $\theta 1$) relative to the in-vivo image P and the gravity direction G, to an external device by wireless communication. Meanwhile, the display unit 4 displays the in-vivo image P taken by the capsule medical apparatus 2 and the current position information of the capsule medical apparatus 2 inside the subject 1. The display unit 4 displays the in-vivo image P in such a manner that the direction (Y axis direction) of the in-vivo image P corresponding to the in-and-out direction D of the obtaining unit 23a and the vertical direction of the display screen are matched.

A user such as a doctor and a nurse operates the operating unit 7 or the input unit 8 while referring to the information (the in-vivo image, the current position information, etc.) displayed on the display unit 4, to guide the capsule medical apparatus 2 to a desirable internal body part (a stomach, a small intestine, a large intestine, etc.) inside the subject 1. The user determines whether a treatment target such as a lesion tissue is present by observing the in-vivo image P displayed on the display unit 4. When the user finds a living tissue for which treatment is required in the in-vivo image P displayed on the display unit 4, the user operates the input unit 8 as described above to select the treatment target from this in-vivo image P.

The external control unit 10 controls the magnetically guiding unit 5 and the power supply unit 6, and determines a relative distance between the living tissue inside the subject 1 being the treatment target that is selected from the in-vivo image P and the treating unit 23. The external control unit 10 controls the positioning of the treating unit 23 with respect to the treatment target in the direction of the center axis CL and the rotation direction based on the determined relative distance and the angle detected by the gravity sensor 24.

Figure 4:
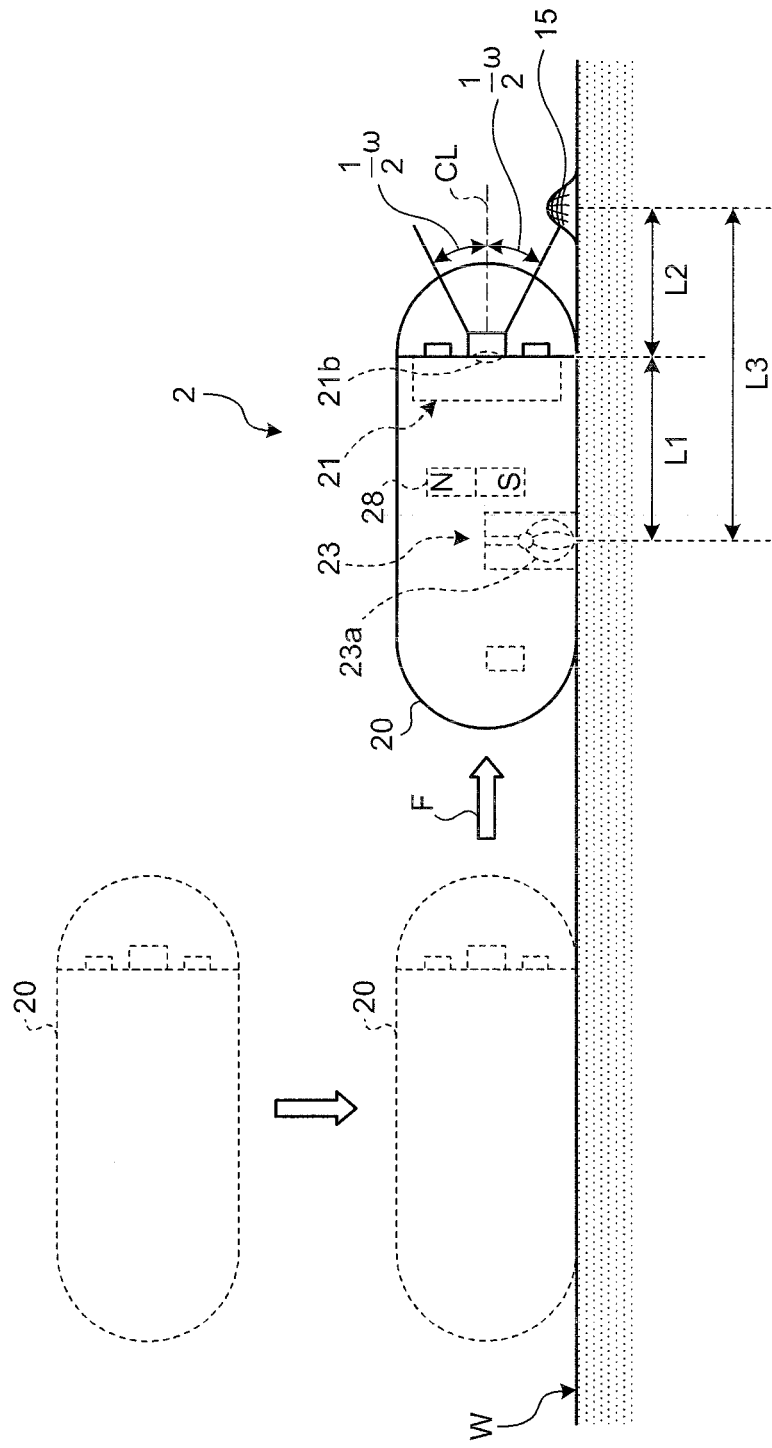
FIG. 4 is a schematic diagram showing a state where the capsule medical apparatus is guided to a specific position inside a subject.
Figure 5:
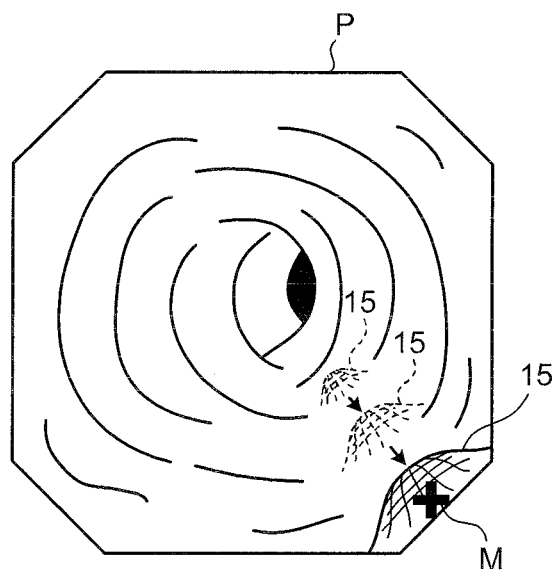
FIG. 5 is a schematic diagram showing an in-vivo image that is taken by the capsule medical apparatus while the apparatus is guided to the specific position inside the subject.

Subsequently, operation performed by the capsule medical system 11 from guidance of the capsule medical apparatus 2 to a specific position inside the subject 1 at which the in-vivo image P showing the treatment target at an edge portion of an image can be imaged, to determination of the relative distance between the treating unit 23 of the capsule medical apparatus 2 and the treatment target is explained. FIG. 4 is a schematic diagram showing a state where the capsule medical apparatus 2 is guided to a specific position inside the subject 1. FIG. 5 is a schematic diagram showing the in-vivo image P that is taken by the capsule medical apparatus 2 while the apparatus is guided to a specific position inside the subject 1. In FIGS. 4 and 5, a lesion tissue 15 is shown as one example of a living tissue being the treatment target. The operation of the capsule medical system 11 is explained referring to FIGS. 4 and 5 below.

When the lesion tissue 15 being the treatment subject inside the subject 1 is selected from the in-vivo image P by the input operation of the input unit 8, the external control unit 10 controls the magnetically guiding unit 5 and the power supply unit 6. Thus, the external control unit 10 maintains the capsule medical apparatus 2 in a state where the in-vivo image P showing the lesion tissue 15 can be taken, and meanwhile, magnetically guides the capsule medical apparatus 2 to a specific position inside the subject 1 at which the in-vivo image P showing the lesion tissue 15 at an edge portion can be imaged.

If the capsule medical apparatus 2 inside the subject 1 is not in contact with an organ internal wall W (for example, in a floating state with liquid inside an organ or the like), the control unit 10 controls the external magnetic field formed by the magnetically guiding unit 5, to bring the capsule medical apparatus 2 into contact with the organ internal wall W by a magnetic force of this external magnetic field. The control unit 10 determines similarity among sequential frames of the in-vivo image P sequentially imaged by the imaging unit 21 of the capsule medical apparatus 2, and when the similarity is low, it is determined that the capsule medical apparatus 2 is not in contact with the organ internal wall W yet. In this case, the control unit 10 continues the control of the external magnetic field formed by the magnetically guiding unit 5 so as to bring the capsule medical apparatus 2 into contact with the organ internal wall W. On the other hand, when the similarity is high, that is, when variation of the in-vivo image P is small among the sequential frames, it is determined that the capsule medical apparatus 2 is in contact with the organ internal wall W. In this case, the control unit 10 controls the external magnetic field formed by the magnetically guiding unit 5 so as to bring the capsule medical apparatus 2 to the specific position described above in a state of contact with the organ internal wall W.

The capsule medical apparatus 2 that is magnetically guided as described contacts with the organ internal wall W, reaches the specific position in a state where the capsule medical apparatus 2 is in contact with the organ internal wall W, and stops at this specific position, maintaining a sate where the lesion tissue 15 is captured inside the imaging field of view of the imaging unit 21, as shown in FIG. 4.

In detail, in the capsule medical apparatus 2, the magnet 28 acts according to the external magnetic field formed by the magnetically guiding unit 5. Thus, the magnet 28 brings the capsule casing 20 of the capsule medical apparatus 2 in contact with the organ internal wall W, and moves (forward) the capsule medical apparatus 2 in the imaging direction F of the imaging unit 21 while maintaining the contact state between the organ internal wall W and the capsule casing 20. The magnet 28 moves the capsule medical apparatus 2 to a vicinity of the lesion tissue 15, and stops the capsule medical apparatus 2 at a position at which a boundary of the imaging field of view of the imaging unit 21 and the lesion tissue 15 intersect, that is, the specific position described above. At this specific position, the magnet 28 pushes the capsule casing 20 onto the organ internal wall W by the magnetic force of the external magnetic field to fix the capsule medical apparatus 2 on the organ internal wall W.

In a period during the capsule medical apparatus 2 thus travels inside the subject 1 to reach the specific position, the imaging unit 21 sequentially images the in-vivo image P showing the lesion tissue 15. The position of the lesion tissue 15 in the in-vivo image P changes from an inner side of the image toward the image edge portion as shown in FIG. 5. The external display unit 4 displays the in-vivo image P showing the lesion tissue 15, and displays a mark M indicating that it is a treatment target selected by the input unit 8, on an image of the lesion tissue 1 in a superimposed manner 5. The mark M corresponds to the position coordinate information of the lesion tissue 15 in the biaxial rectangular coordinate system of the display unit 4. The control unit 10 determines that the capsule medical apparatus 2 has reached the specific position described above when the mark M on the image of the lesion tissue 15 is positioned at the image edge portion of the in-vivo image P, and controls the capsule medical apparatus 2 to stop at this specific position.

On the other hand, the distance determining unit 10d described above determines a relative distance L3 of the treating unit 23 of the capsule medical apparatus 2 to lesion tissue 15 when the capsule medical apparatus 2 stops at the specific position inside the subject 1 as shown in FIG. 4. The specific position that the capsule medical apparatus 2 reaches is the position inside the subject 1 at which the in-vivo image P showing the lesion tissue 15 at the image edge portion can be imaged as described above, and is the position at which the boundary of the imaging field of view of the imaging unit 21 and the lesion tissue 15 intersect, as shown in FIG. 4. When the capsule medical apparatus 2 stops at the specific position, the relative distance between the lesion tissue 15 and the imaging unit 21 (specifically, the optical system 21b) is to be a specific distance L2 that is defined by the angle of view ω of the imaging unit 21 and an outer diameter r of the capsule casing 20. Moreover, the relative distance between the imaging unit 21 and the treating unit 23, specifically, an inter-parts distance L1 between the optical system 21b and the obtaining unit 23a is fixed inside the capsule casing 20. The distance determining unit 10d has a relative distance L3 that is a sum of the inter-parts distance L1 and the specific distance L2 in advance, as a known data, and determines the relative distance L3 between the lesion tissue 15 and the obtaining unit 23a when the capsule medical apparatus 2 stops at the specific position in contact with the organ internal wall W.

The specific distance L2 described above can be calculated by the following Equation (1) using the angle of view ω of the imaging unit 21 and the outer diameter r of the capsule casing 20.

$$L2=(r/2)/\tan(\omega/2) \tag{1}$$

Figure 6:
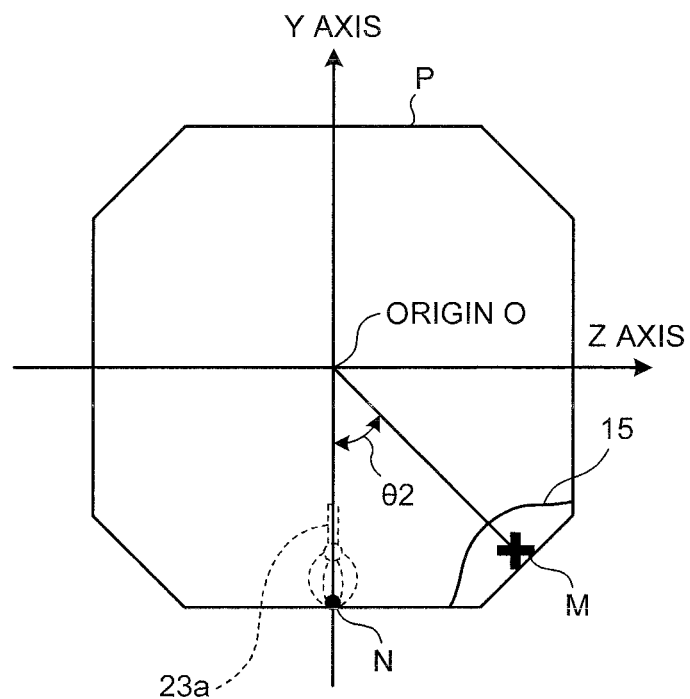
FIG. 6 is a schematic diagram for explaining a calculation processing of a rotation angle performed by an angle calculator.

Next, operation of the angle calculator 10e that calculates the rotation angle of the capsule medical apparatus 2 relative to a treatment target is explained using the lesion tissue 15 as one example of the treatment target. FIG. 6 is a schematic diagram for explaining a calculation processing of the rotation angle performed by the angle calculator 10e. FIG. 6 schematically shows the in-vivo image P that is displayed on the display unit 4 when the angle calculator 10e calculates a rotation angle θ2 of the capsule medical apparatus 2.

In the external display unit 4, a biaxial rectangular coordinate system, that is, the biaxial rectangular coordinate system with the Y axis and the Z axis as shown in FIG. 6, similar to that of the in-vivo image P is set, and the vertical direction of the display unit 4 coincides with the Y axis and the horizontal direction of the display unit 4 coincides with the Z axis. The display unit 4 in which the biaxial rectangular coordinate system with the Y axis and the Z axis displays the mark M that indicates the position coordinates of the lesion tissue 15 in this biaxial rectangular coordinate system, on the image of the lesion tissue 15.

The angle calculator 10e obtains position coordinate information of the lesion tissue 15 input by the input unit 8, that is, position coordinate information of the mark M in the biaxial rectangular coordinate system of the display unit 4. Furthermore, the angle calculator 10e has position coordinate information of the obtaining unit 23a in the biaxial rectangular coordinate system of the display unit 4 in advance as position coordinate information of a known point N (for example, a negative point) on the Y axis. The angle calculator 10e calculates the rotation angle θ2 that is formed between the direction of the treating unit of the capsule medical apparatus 2 and the direction of the lesion tissue 15 based on the Y axis direction (specifically, a negative direction of the Y axis) in the biaxial rectangular coordinate system of the display unit 4 and the position coordinate information of the lesion tissue 15.

In detail, the angle calculator 10e calculates respective position vectors of the mark M and the point N having the initial point at the origin O. An angle formed between the two position vectors is substantially equivalent to an angle formed between a direction of a perpendicular connecting an arbitrary point on the center axis CL of the capsule medical apparatus 2 and the lesion tissue 15 (direction of the treatment target relative to the capsule medical apparatus 2) and a direction of the treating unit 23 (the in-and-out direction D of the obtaining unit 23a). The angle calculator 10e calculates an angle formed between the two position vectors, that is, the rotation angle θ2 between the direction of the treating unit of the capsule medical apparatus 2 and the direction of the lesion tissue 15, based on the respective position vectors of the mark M and the point N. The rotation angle θ2 calculated by the angle calculator 10e is a rotation angle of the capsule medical apparatus 2 that is required to position the lesion tissue 15 in the in-and-out direction D of the obtaining unit 23a.

Figure 7:
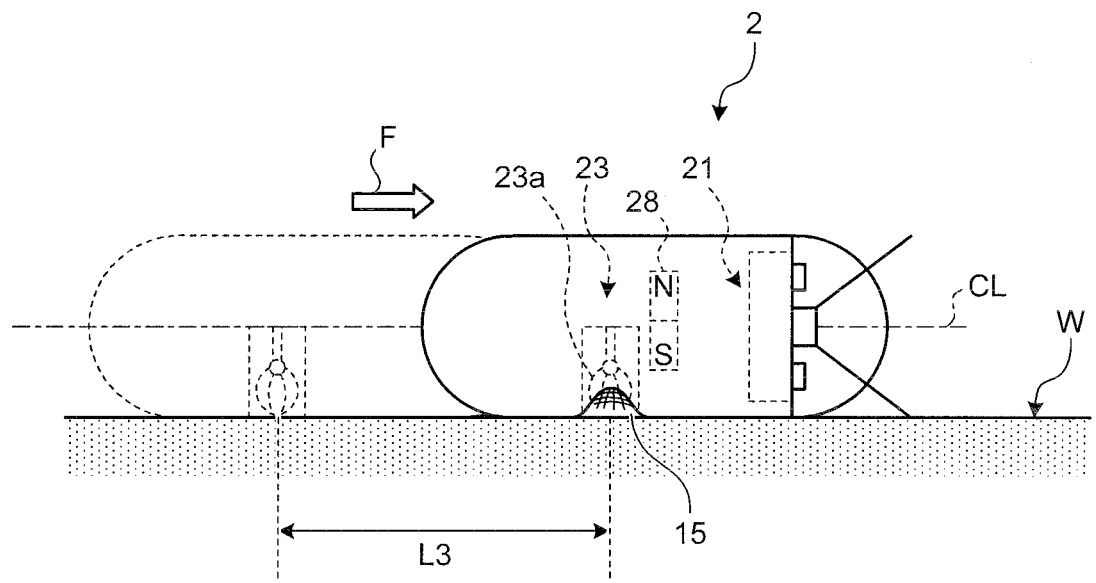
FIG. 7 is a schematic diagram for explaining positioning of a treating unit and a lesion tissue in a longitudinal direction of the capsule medical apparatus.
Figure 8:
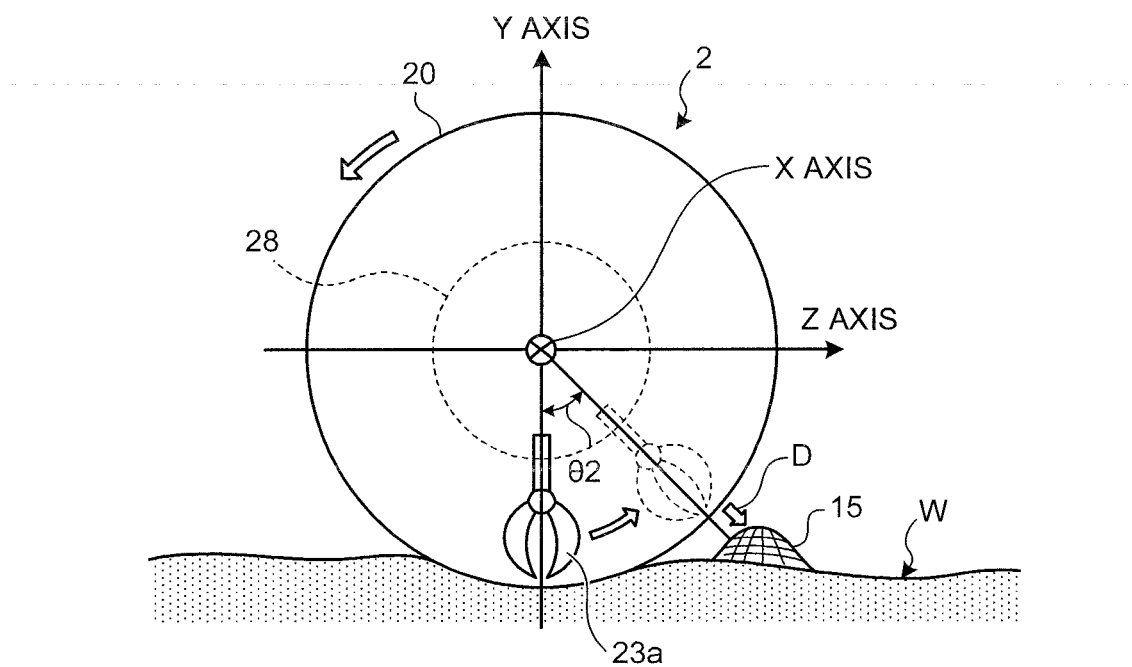
FIG. 8 is a schematic diagram for explaining positioning of the treating unit and the lesion tissue in a rotational direction of the capsule medical apparatus.

Next, operation of the capsule medical system 11 at the time of positioning of the obtaining unit 23 of the capsule medical apparatus 2 with a treatment target is explained using the lesion tissue 15 as one example of the treatment target. FIG. 7 is a schematic diagram for explaining the positioning of the treating unit 23 and the lesion tissue 15 in the longitudinal direction of the capsule medical apparatus 2. FIG. 8 is a schematic diagram for explaining the positioning of the treating unit 23 and the lesion tissue 15 in a rotational direction of the capsule medical apparatus 2.

The position control unit 10a controls the external magnetic field formed by the magnetically guiding unit 5 based on the relative distance L3 between the treating unit 23 and the lesion tissue 15 determined by the distance determining unit 10d. Thus, the position control unit 10a moves the capsule medical apparatus 2 in the imaging direction F of the imaging unit 21 by the relative distance L3 while maintaining the state where the capsule medical apparatus 2 and the organ internal wall W contact with each other. The capsule medical apparatus 2 travels (forward) in the imaging direction F (that is, the direction of the center axis CL) by the relative distance L3 while maintaining the state of contact with the organ internal wall W, as shown in FIG. 7, by the effect of the magnet 28 that acts according to the external magnetic field. As a result, the capsule medical apparatus 2 can achieve highly accurate positioning of the obtaining unit 23a of the treating unit 23 and the lesion tissue 15 in the direction of the center axis CL (that is, the X axis in the triaxial rectangular coordinate system of the capsule medical apparatus 2) in the longitudinal direction of the capsule casing 20.

On the other hand, the position control unit 10a controls the external magnetic field formed by the magnetically guiding unit 5 based on the rotation angle θ2 between the in-and-out direction D of the obtaining unit 23a and the direction of the lesion tissue 15 that is calculated by the angle calculator 10e, thereby rotating the capsule medical apparatus 2 by the rotation angle θ2 about the X axis described above, while maintaining the state where the capsule medical apparatus 2 and the organ internal wall W contact with each other. The capsule medical apparatus 2 rotates about the X axis (that is, about the center axis CL) by the rotation angle θ2 while maintaining the state of contact with the organ internal wall W as shown in FIG. 8, by the effect of the magnet 28 that acts according to the external magnetic field. As a result, the capsule medical apparatus 2 can achieve highly accurate positioning of the obtaining unit 23a of the treating unit 23 and the lesion tissue 15 in the rotation direction about the center axis CL of the capsule casing 20.

The position control unit 10a first controls the positioning of the treating unit 23 and the lesion tissue 15 in the longitudinal direction of the capsule medical apparatus 2. Thereafter, the position control unit 10a can control the positioning of the treating unit 23 and the lesion tissue 15 in the rotation direction about the center axis CL. Alternatively, the position control unit 10a can first controls the positioning of the treating unit 23 and the lesion tissue 15 in the rotation direction about the center axis CL, and then control the positioning of the treating unit 23 and the lesion tissue 15 in the longitudinal direction of the capsule medical apparatus 2. Alternatively, the position control unit 10a can control the positioning of the treating unit 23 and the lesion tissue 15 in both the longitudinal direction and the rotation direction at the same time.

The capsule medical apparatus 2 for which the positioning of the treating unit 23 and the lesion tissue 15 has been completed as described above brings the lesion tissue 15 in the in-and-out direction D of the obtaining unit 23a. The capsule medical apparatus 2 in such a state obtains a control signal from the external control unit 10 through the external communicating unit 3, and causes the obtaining unit 23a to perform a series of the obtaining operation based on this obtained control signal, and accurately excises and obtains the lesion tissue 15 from an internal body part of the subject 1 with this obtaining unit 23a. The capsule medical apparatus 2 keeps the obtained lesion tissue 15 inside the capsule casing 20.

Thereafter, the capsule medical apparatus 2 that holds the lesion tissue 15 is moved to travel inside a digestive canal by peristaltic movement or the effect of the external magnetic field and the like, and is finally discharged out of the subject 1. The lesion tissue 15 inside the capsule medical apparatus 2 discharged out of the subject 1 can be collected by a doctor, nurse, or the like, and can be used for a biopsy or the like.

Figure 9:
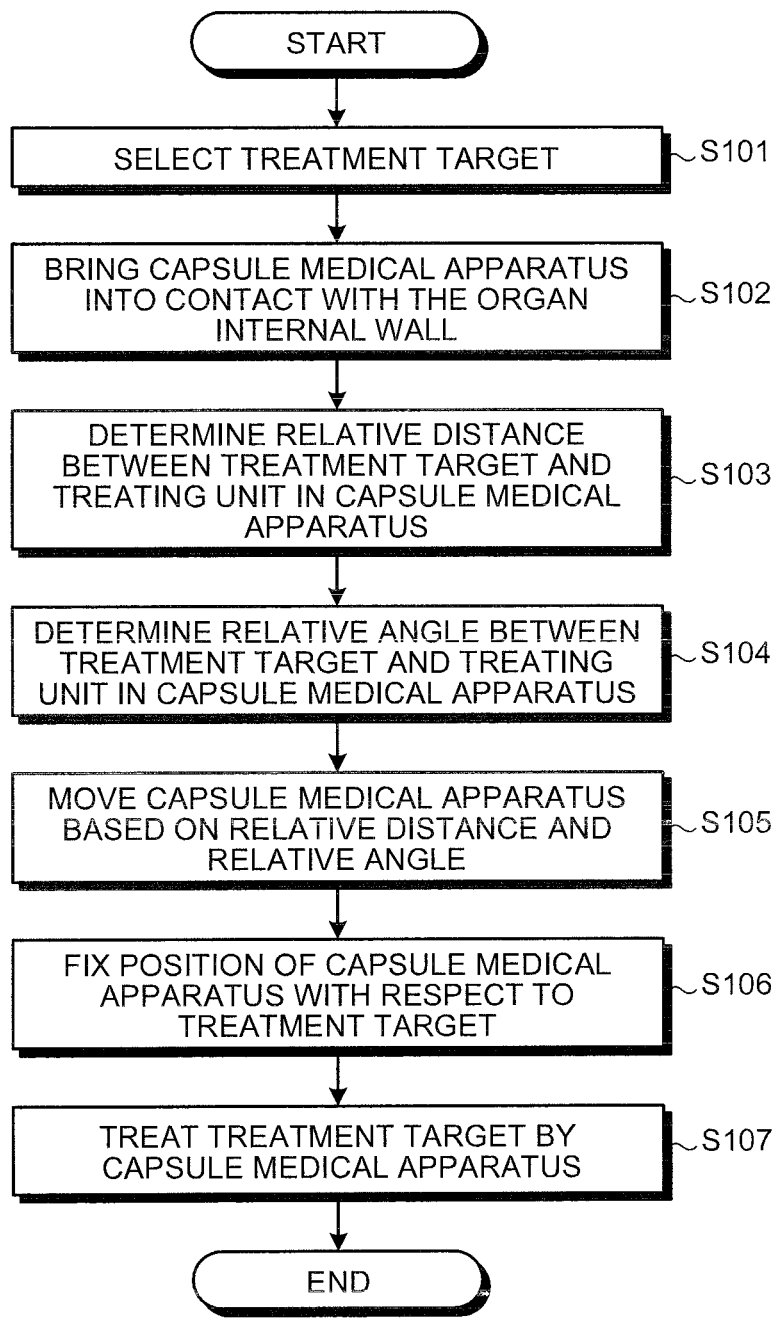
FIG. 9 is a flowchart illustrating a procedure for treating a desired region inside a subject with the capsule medical apparatus.

Next, a procedure for treating a desired region inside the subject with the capsule medical apparatus 2 is explained. FIG. 9 is a flowchart illustrating the procedure for treating the desired region inside the subject with the capsule medical apparatus 2 according to the first embodiment of the present invention.

As shown in FIG. 9, the user first selects a treatment target (Step S101). At Step S101, selecting the treatment target is realized in which the lesion tissue 15 as being the treatment target is selected from the in-vivo image P by input operation through the input unit 8. After that, the control unit 10 brings the capsule medical apparatus 2 into contact with the organ internal wall W of the subject 1 (Step S102). Then, the control unit 10 controls an external magnetic field by the magnetically guiding unit 5 so that the magnetic force of the external magnetic field brings the capsule medical apparatus 2 into the organ internal wall W.

After that, the distance determining unit 10d determines the relative distance L3 between the selected treatment target and the treating unit 23 in the capsule medical apparatus 2 (Step S103). At Step S103, the distance determining unit 10d determines the relative distance L3 obtained as a sum of the inter-parts distance L1 and the specific distance L2.

The angle calculator 10e then determines a relative angle between the treatment target and the treating unit 23 in the capsule medical apparatus 2 (Step S104). At Step S104, the angle calculator 10e calculates a rotation angle θ2, which is a relative angle between the direction of treating unit 23 in the capsule medical apparatus 2 and the direction of the lesion tissue 15, based on the position coordinate information of the Y axis and the lesion tissue 15 in the biaxial rectangular coordinate system of the display unit 4.

The position controller 10a then moves the capsule medical apparatus 2 based on the relative distance and the relative angle (Step S105). At Step S105, the position controller 10a moves capsule medical apparatus 2 by the relative distance L3 and the rotation angle θ2, thereby achieving position adjustment of the treating unit 23 and the lesion tissue 15.

The control unit 10 then fixes the position of the capsule medical apparatus 2 with respect to the treatment target (Step S106). At Step S106, the magnet 28 pushes, at the position where the position adjustment of the treating unit 23 and the lesion tissue 15 is achieved, the capsule casing 20 onto the organ internal wall W by the magnetic force of the external magnetic field to fix the capsule medical apparatus 2 on the organ internal wall W.

After that, the control unit 10 treats the treatment target by the capsule medical apparatus 2 (Step S107). At Step S107, the control unit 10 causes the obtaining unit 23a to excise and obtain the lesion tissue 15 from the internal body part of the subject 1, and then causes the obtaining unit 23a to store the obtained lesion tissue 15 inside the capsule casing 20. The control unit 10 then ends the above procedure.

As explained above, in the first embodiment, the distance determining unit determines the relative distance between the treating unit of the capsule medical apparatus and a treatment target. The angle calculator calculates the rotation angle between the direction of this treatment target and the treating unit direction. The position control unit causes the capsule medical apparatus to travel in the imaging direction by the relative distance between this treating unit and the treatment target by using the magnet arranged inside the capsule medical apparatus, and to rotate by this rotation angle. Therefore, highly accurate positioning of the treating unit of the capsule medical apparatus that gives treatment to a desirable living tissue inside a subject and the living tissue being the treatment target is possible, and therefore, the living tissue being the treatment target can be accurately positioned in the treating unit direction of the capsule medical apparatus. As a result, it is possible to realize a capsule medical system that is capable of accurately performing treatment on a living tissue being a treatment target with a simple configuration, without using a medical device that can observe a state inside a subject such as an X-ray device.

Next, a second embodiment of the present invention is explained. In the first embodiment described above, the relative distance between the treatment target and the treating unit 23 whose position can be identified in a state where the capsule medical apparatus 2 stays at the specific position inside the subject 1 is fixed. In the second embodiment, a distance between the treatment target and the imaging unit is measured by the capsule medical apparatus, and by adding the measured distance and the inter-parts distance between the imaging unit and the treating unit, the relative distance between the treating unit and the treatment target is calculated.

Figure 10:
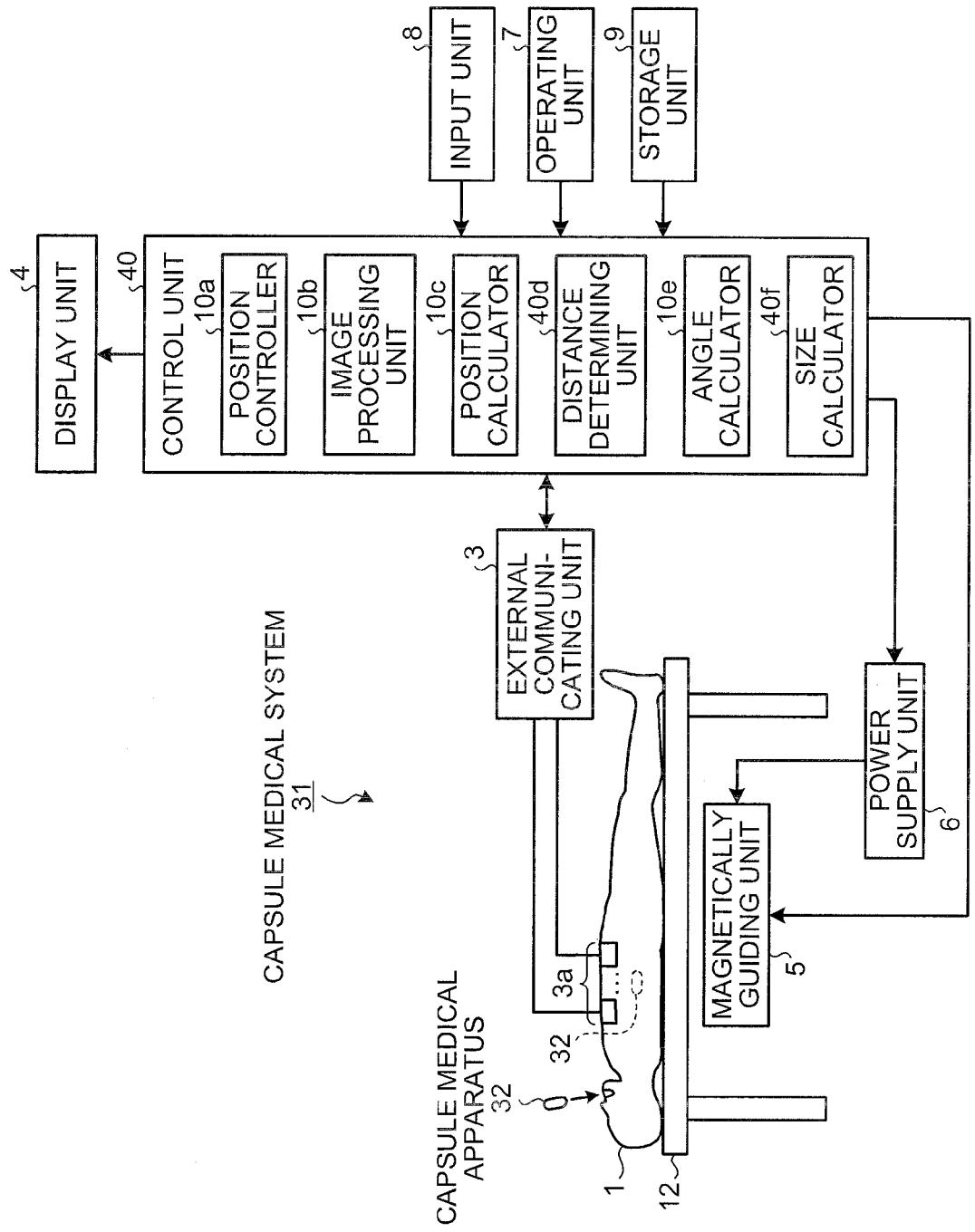
FIG. 10 is a block diagram schematically showing a configuration example of a capsule medical system according to a second embodiment of the present invention.

FIG. 10 is a block diagram schematically showing a configuration example of a capsule medical system according to a second embodiment of the present invention. As shown in FIG. 10, a capsule medical system 31 has a capsule medical apparatus 32 in place of the capsule medical apparatus 2 according to the first embodiment described above, and a control unit 40 in place of the control unit 10. Other components are the same as those of the first embodiment, and like reference characters refer to like parts.

The capsule medical apparatus 32 is a medical apparatus in a capsule shape that is formed in a size small enough to be introduced inside the subject 1, and has a distance measuring function for measuring a distance between a treatment target inside the subject 1 and the imaging unit. The capsule medical apparatus 32 transmits a result of this distance measurement to the external communicating unit 3 placed outside by the wireless communication function described above. Other functions of the capsule medical apparatus 32 are the same as those of the capsule medical apparatus 2 according to the first embodiment described above.

When a treatment target is selected by the input unit 8 from the in-vivo image P displayed on the display unit 4, the control unit 40 generates a control signal to instruct measurement of the distance to this treatment target, and controls the external communicating unit 3 to transmit this generated control signal to the capsule medical apparatus 32 inside the subject 1. Furthermore, the control unit 40 controls a position and an orientation of the capsule medical apparatus 2 by controlling the magnetically guiding unit 5 and the power supply unit 6, thereby bringing the treatment target in a distance measurement area of the capsule medical apparatus 32. In other words, the control unit 40 controls the capsule medical apparatus 32 to be arranged in such an orientation enabling the measurement of the distance to the treatment target based on the instruction information input by the input unit 8.

Furthermore, the control unit 40 includes the position controller 10a, the image processing unit 10b, the position calculator 10c, the angle calculator 10e, and a size calculator 40f. The control unit 40 further includes a distance determining unit 40d in place of the distance determining unit 10d of the capsule medical system 11 according to the first embodiment. The distance determining unit 40d determines the relative distance L3 between the treating unit (specifically, the obtaining unit 23a) of the capsule medical apparatus 32 and the treatment target, using the result of distance measurement obtained from the capsule medical apparatus 32. The position control unit 10a causes the capsule medical apparatus 32 to travel by the relative distance L3 determined by the distance determining unit 40d, thereby controlling the positioning of the treatment target and the treating unit 23 of the capsule medical apparatus 32 highly accurately. In this case, it is not required for the control unit 40 to magnetically introduce the capsule medical apparatus 32 to the specific position described above.

The size calculator 40f calculates the size of the living tissue being the treatment target that is selected from the in-vivo image P based on the position coordinate information input by the input unit 8 and the result of the distance measurement performed by the capsule medical apparatus 32. The control unit 40 causes the display unit 4 to display a result of calculation by the size calculator 40f. The size of a living tissue calculated by the size calculator 40f includes, for example, a perimeter, an outer diameter, and an area of a living tissue. Other functions of the control unit 40 are the same as those of the control unit 10 of the capsule medical system 11 according to the first embodiment described above.

Figure 11:
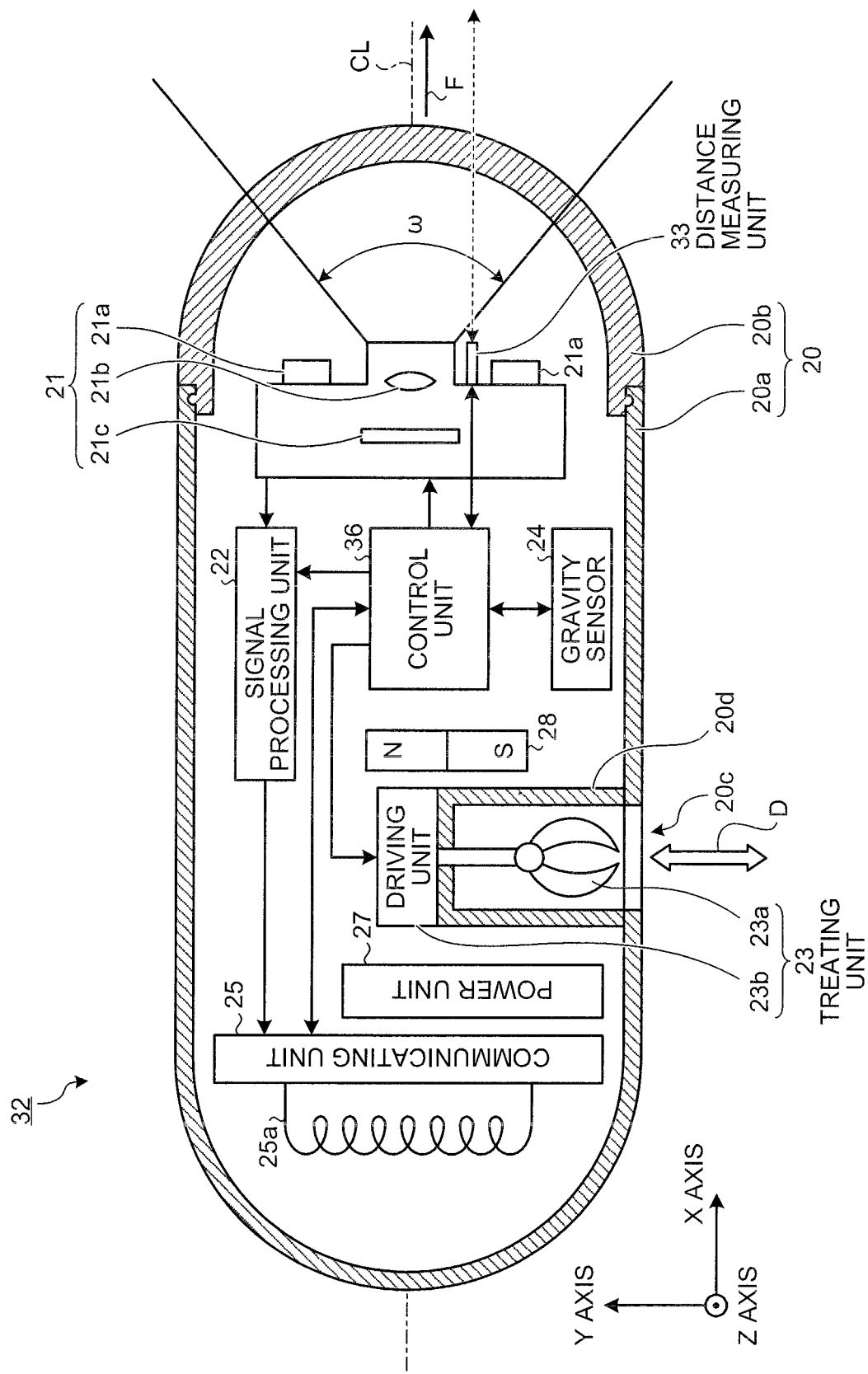
FIG. 11 is a schematic diagram showing a configuration example of a capsule medical apparatus according to the second embodiment of the present invention.

Next, a configuration of the capsule medical apparatus 32 according to the second embodiment is explained. FIG. 11 is a schematic diagram showing a configuration example of the capsule medical apparatus according to the second embodiment of the present invention. As shown in FIG. 11, the capsule medical apparatus 32 according to the second embodiment has a control unit 36 in place of the control unit 26 of the capsule medical apparatus 2 according to the first embodiment, and further includes a distance measuring unit 33 that measures a distance between a treatment target and the imaging unit 21. The communicating unit 25 transmits a result of measurement performed by the distance measuring unit 33 to the external communicating unit 3 based on a control of the control unit 36. Other components thereof are the same as those of the first embodiment, and like reference characters refer to like parts.

The distance measuring unit 33 irradiates light (for example, an infra-red ray beam, a visible light beam, etc.) in a predetermined wavelength range on a treatment target that is positioned in the imaging direction F of the imaging unit 21 (that is, a treatment target positioned in the imaging field of view of the imaging unit 21) through the dome-shaped casing 20b, and receives reflected light from the treatment target. The distance measuring unit 33 measures a distance between the living tissue being this treatment target and the imaging unit 21 (for example, the optical system 21b) based on a trigonometry or the like using a result of receiving the reflected light. The distance measuring unit 33 transmits a result of the distance measurement between the treatment target and the imaging unit 21 to the control unit 36.

The distance measuring unit 33 can be arranged inside the capsule casing 20 independent from the imaging unit 21, and can be an autofocus mechanism that is provided in the imaging unit 21. In this case, the distance measuring unit 33 as the autofocus mechanism of the imaging unit 21 measures the distance between the living tissue being the treatment target and the imaging unit 21 based on a trigonometry using light transmission and reception of an LED beam or an infra-red ray beam, or based on an amount of movement of a lens in the optical system 21b. Alternatively, the distance measuring unit 33 can measure the distance between the treatment target and the imaging unit 21 by outputting an ultrasonic wave to the treatment target and based on an echo of this ultrasonic wave.

The control unit 36 controls the distance measuring unit 33 based on a control signal from the external control unit 40 described above, and obtains a result of the measurement by this distance measuring unit 33. In this case, the control unit 36 causes the distance measuring unit 33 to perform distance measurement operation at such timing that the living tissue being the treatment target is positioned inside the distance measurement area of the distance measuring unit 33, as a result, the measurement distance between this living tissue and the imaging unit 21 is obtained. The control unit 36 controls the communicating unit 25 to transmit the result of the measurement by the distance measuring unit 33 to the external communicating unit 3 by wireless communication. Other functions of the control unit 36 are the same as those of the control unit 26 of the capsule medical apparatus 2 according to the first embodiment.

Figure 12:
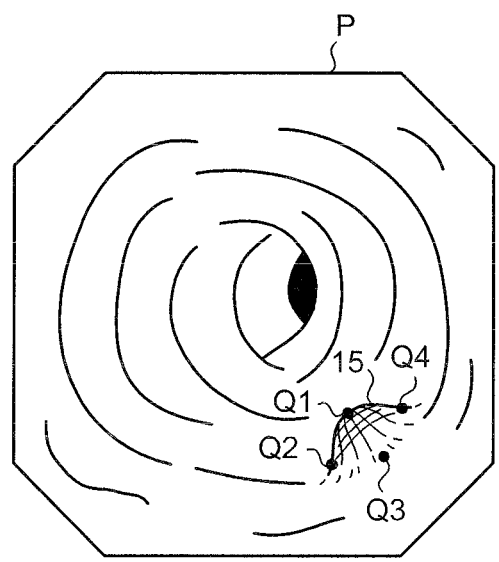
FIG. 12 is a schematic diagram showing an in-vivo image that is displayed on a display unit when selection of a lesion tissue is made.
Figure 13:
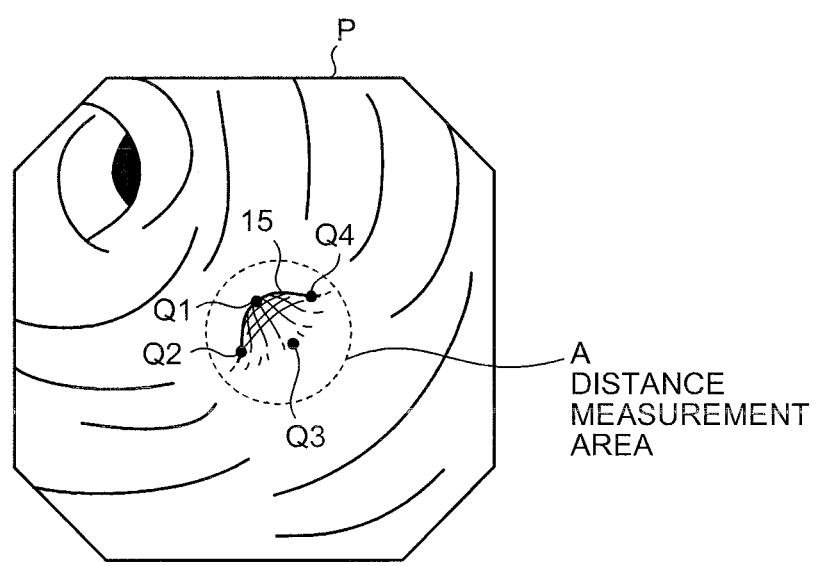
FIG. 13 is a schematic diagram showing an in-vivo image that is displayed on the display unit when the capsule medical apparatus measures a distance to a lesion tissue.
Figure 14:
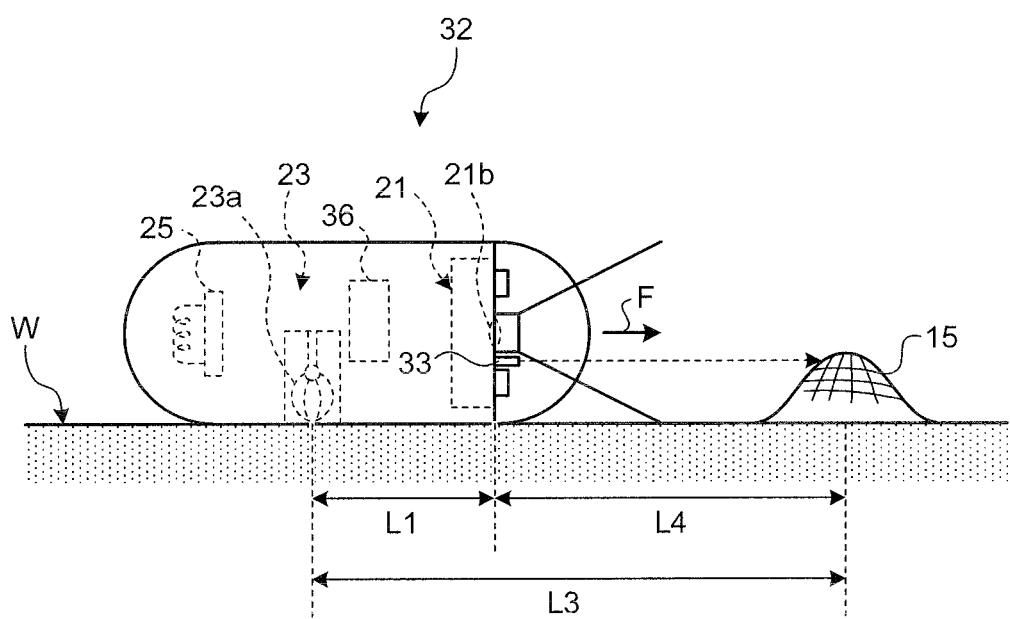
FIG. 14 is a schematic diagram for explaining relative distance between the treating unit of the capsule medical apparatus according to the second embodiment and a lesion tissue.

Next, operation of the capsule medical system 31 until the relative distance L3 between the treatment target inside the subject 1 and the treating unit 23 of the capsule medical apparatus 32 is determined is explained, using the lesion tissue 15 as one example of the living tissue being the treatment target. FIG. 12 is a schematic diagram showing an in-vivo image that is displayed on the display unit when selection of the lesion tissue is made. FIG. 13 is a schematic diagram showing an in-vivo image that is displayed on the display unit when the capsule medical apparatus measures a distance to the lesion tissue. FIG. 14 is a schematic diagram for explaining a relative distance between the treating unit of the capsule medical apparatus according to the second embodiment and the lesion tissue.

When the lesion tissue 15 being the treatment target is selected from the in-vivo image P displayed on the display unit 4, a user performs input operation such as click using the input unit 8, to specify a plurality of coordinate points so as to surround the lesion tissue 15 in the in-vivo image P. In response to the input operation, the input unit 8 inputs, for example, respective position coordinate information of four coordinate points Q1 to Q4 surrounding the image of the lesion tissue 15 to the control unit 40 as shown in FIG. 12. This means that the input unit 8 has selected the lesion tissue 15 that is surrounded by the coordinate points Q1 to Q4 from the in-vivo image P. Coordinate points input by the input unit 8 when the lesion tissue 15 is selected from the in-vivo image P are only required to surround the image of the lesion tissue 15 with a plurality of points, and the number thereof is not limited to four.

As shown in FIG. 12, when the lesion tissue 15 is selected from the in-vivo image P, the control unit 40 controls the external magnetic field formed by the magnetically guiding unit 5 described above, to bring the capsule medical apparatus 32 in an orientation enabling measurement of the distance to the lesion tissue 15 inside the subject 1. As a result, the lesion tissue 15 inside the subject 1 is positioned inside a distance measurement area A of the distance measuring unit 33 described above, as shown in FIG. 13. The control unit 40 recognizes that the capsule medical apparatus 32 is in such an orientation that the distance to the lesion tissue 15 can be measured based on pixel information of the in-vivo image P in which the lesion tissue 15 is positioned inside the distance measurement area A. The control unit 40 controls the capsule medical apparatus 32 to maintain such orientation, and meanwhile, controls the external communicating unit 3 to transmit a control signal to instruct the distance measurement to the capsule medical apparatus 32.

The capsule medical apparatus 32 inside the subject 1 measures the distance to the lesion tissue 15 based on the control signal from the control unit 40. In the capsule medical apparatus 32, the control unit 36 causes the distance measuring unit 33 to measure the distance based on the control signal from this control unit 40. In this case, the distance measuring unit 33 measures the distance between the lesion tissue 15 that is positioned in the imaging direction F of the imaging unit 21 as shown in FIG. 14 and the imaging unit 21 (specifically, the optical system 21b), and notifies a measurement distance L3 to the control unit 36. The control unit 36 obtains the result (the measurement distance L4) of measurement by the distance measuring unit 33, and controls the communicating unit 25 to transmit this obtained measurement distance L4 to the external communicating unit 3.

The external control unit 40 obtains the result (the measurement distance L4) of measurement by the distance measuring unit 33 through the external communicating unit 3. The size calculator 40f calculates the actual size (for example, the perimeter, the outer diameter, the area, etc.) of the lesion tissue 15 based on the respective position coordinate information of the coordinate points Q1 to Q4 (see FIG. 13) input by the input unit 8 and the measurement distance L4. The control unit 40 causes the display unit 4 to display a graphical user interface (GUI) (not shown) for choosing whether the lesion tissue 15 is the treatment target, together with the size of the lesion tissue 15 calculated by the size calculator 40f. A user checks the size of the lesion tissue 15 displayed on the display unit 4, and determines whether this lesion tissue 15 is a treatment target (that is, a living tissue requiring treatment).

When the lesion tissue 15 is a treatment target, the input unit 8 inputs selection information indicating that the lesion tissue 15 is a treatment target, to the control unit 40. The distance determining unit 40d determines the relative distance L3 between the lesion tissue 15 corresponding to the selection information and the treating unit 23 of the capsule medical apparatus 32. Specifically, the distance determining unit 40d calculates the relative distance L3 between the lesion tissue 15 and the treating unit 23 of the capsule medical apparatus 32 by adding the result (the measurement distance L4) of measurement by the distance measuring unit 33 obtained from the capsule medical apparatus 32 and the inter-parts distance L1 described above (see FIG. 14).

The position control unit 10a controls the external magnetic field formed by the magnetically guiding unit 5 based on the relative distance L3 calculated by the distance determining unit 40d. Thus, the position control unit 10a moves the capsule medical apparatus 32 in the imaging direction F of the imaging unit 21 by the relative distance L3, while maintaining the contact state between the capsule medical apparatus 32 and the organ internal wall W. The position control unit 10a once stops the capsule medical apparatus 32 at the time when the capsule medical apparatus 32 is positioned at the position at which the boundary of the imaging field of view of the imaging unit 21 and the lesion tissue 15 intersect, that is, the specific position described above. The control unit 40 causes the display unit 4 to display GUI for requesting input of position coordinate information that is required for the calculation of the rotation angle θ2 of the capsule medical apparatus 32 relative to the lesion tissue 15. The input unit 8 inputs position coordinate information of the lesion tissue 15 shown at the image edge portion of the in-vivo image P to the control unit 40 according to input operation by a user. The angle calculator 10e calculates the rotation angle θ2 similarly to the case of the first embodiment described above. Thereafter, the position control unit 10a controls the external magnetic field formed by the magnetically guiding unit 5 in a similar manner as the case of the first embodiment, and as a result, highly accurately controls the positioning of the treating unit 23 (in detail, the obtaining unit 23a) of the capsule medical apparatus 32 and the lesion tissue 15 in the direction of the center axis CL and the rotation direction.

On the other hand, when the lesion tissue 15 is not a treatment target, the input unit 8 inputs selection information indicating that the lesion tissue 15 is not a treatment target to the control unit 40. In this case, the control unit 40 cancels the coordinate points (Q1 to Q4 shown in FIGS. 12 and 13) surrounding the image of the lesion tissue 15, and causes the display unit 4 to display information indicating a request of input of coordinate points to newly select a treatment target from the in-vivo image P. The control unit 40 repeats the operation (control) for the positioning of this treatment target and the capsule medical apparatus 32 when a plurality of coordinate points to select the treatment target are input.

As described, in the second embodiment, the distance measuring unit measures the distance between a living tissue that is positioned in the imaging direction of the imaging unit of the capsule medical apparatus and the imaging unit. Moreover, the distance determining unit calculates the relative distance between the treating unit of the capsule medical apparatus in the imaging direction of the in-vivo image and the living tissue being the treatment target by adding the inter-parts distance between the imaging unit and the treating unit and the measurement distance obtained by the distance measuring unit. Furthermore, the position control unit moves the capsule medical apparatus in the imaging direction by the relative distance calculated by the distance determining unit, and other configurations are substantially the same as the first embodiment. Therefore, the distance between the imaging unit and a treatment target can be obtained without using the outer diameter and an external form of the capsule medical apparatus. As a result, similar effect as the first embodiment described above can be produced, and the capsule medical system can be realized that can perform positioning of the desirable treating unit of the capsule medical apparatus and a treatment target even if the outer diameter or the external form of the capsule medical apparatus varies.

Furthermore, the input unit inputs a plurality of coordinate points surrounding a desirable living tissue that is selected from an in-vivo image. The size calculator calculates the actual size of a desirable living tissue based on respective position coordinate information of the coordinate points and the measurement distance (that is, distance between the living tissue and the imaging unit) obtained by the distance measuring unit. Further, the display unit is configured to display a result of calculation by the size calculator. Therefore, the capsule medical system can be realized in which whether the desirable living tissue is a treatment target can be judged, and the positioning of the living tissue (for example, a lesion tissue, etc.) that has been determined as a treatment target and the treating unit can be selectively performed.

In the first and the second embodiments, the capsule medical apparatus having the treating unit that performs obtaining of a living tissue from an internal body part as the treatment given to a living tissue has been explained. However, it is not limited thereto, and the treating unit included in the capsule medical apparatus can be one that injects a medical fluid into a living tissue of an internal body part, one that releases a medicine to a living tissue of an internal body part, one that gives therapy (for example, a laser therapy, and a thermal therapy) to a living tissue such as a lesion tissue, or one that cuts off or crushes a living tissue by ultrasonic oscillation. Alternatively, the treating unit of the capsule medical apparatus can be a detaining unit that detains the capsule medical apparatus at an internal body part to give treatment such as a therapy to a living tissue.

Moreover, while in the first and the second embodiments, the rotation angle θ2 of the capsule medical apparatus relative to a treatment target is calculated, and the capsule medical apparatus is rotated by this rotation angle θ2 to match the in-and-out direction D of the obtaining unit 23a and the direction of a lesion tissue, it is not limited thereto. Specifically, when injection or release of a medicine is performed near a living tissue such as a lesion tissue being a treatment target, a discharge direction of this medicine is not necessarily be required to be matched with the direction of the living tissue. Therefore, if the position of the treating unit and the position of the living tissue being a treatment target are matched in the longitudinal direction (imaging direction) of the capsule medical apparatus, the treatment to this living tissue can be certainly performed. Alternatively, if the capsule medical apparatus is configured to discharge a medicine from the entire periphery of the capsule casing by providing discharge outlets for the medicine at a plurality of positions along a direction of the periphery of the capsule casing, the rotation angle θ2 of the capsule medical apparatus relative to a treatment target is not required to be calculated.

Furthermore, while in the first and the second embodiments, it is determined that the capsule casing is in contact with an organ internal wall when the similarity in images is high between the sequential in-vivo images, that is, when the position of a subject such as an organ inside the subject is substantially stable (scarce change) in the sequential in-vivo images, it is not limited thereto. A contact detecting unit that detects a state where an organ internal wall and the capsule casing are in contact with each other can be provided in the capsule medical apparatus, and the determination whether the organ internal wall and the capsule casing are in contact with each other can be made based on a result of detection by this contact detecting unit. Alternatively, it can be determined that the organ internal wall and the capsule casing 20 are in contact with each other when the capsule medical apparatus is moved toward the organ internal wall for a predetermined time or longer. As a result, the contact state of the organ internal wall and the capsule casing can be surely detected without depending on movement of an organ such as peristaltic movement. The contact detecting unit can be a contact sensor that detects the contact state using an inter-electrode resistance value or a contact pressure, and the like, a potential of hydrogen (pH) sensor, or an optical sensor.

Moreover, while in the first embodiment, the specific distance L2 defined by the angle of view ω of the imaging unit and the outer diameter r of the capsule casing is fixed value, it is not limited thereto. Specifically, the angle of view and the outer diameter of the capsule casing are input corresponding to a type of a capsule medical apparatus, and the specific distance L2 can be calculated based on the input information. In this case, the distance determining unit 10d can calculate the specific distance L2 using Equation (1) described above based on the angle of view ω and the outer diameter r that are input by the input unit 8 for each type of the capsule medical apparatus. As a result, the capsule medical system 11 can perform highly accurate positioning of the treating unit of the capsule medical apparatus and a treatment target, even if the outer diameter or the external form thereof varies.

Furthermore, while in the first embodiment, for a treatment target, the position coordinate information of a single point is input, it is not limited thereto. Similarly to the case of the second embodiment described above, a plurality of coordinate points that surround a living tissue being a treatment target can be input, and the size of the living tissue that is surrounded by these coordinate points can be calculated. In this case, the control unit 10 of the capsule medical system 11 according to the first embodiment includes the size calculator 40f described above, and the size calculator 40f can calculate the actual size of this living tissue based on the respective position coordinate information of the coordinate points surrounding the living tissue being a treatment target and the specific distance L2 when the capsule medical apparatus 2 reaches the specific position (position at which an in-vivo image showing the living tissue as a treatment target at an image edge portion can be taken) inside the subject 1.

Moreover, while in the first and the second embodiments, the magnet is provided inside the capsule medical apparatus, and the capsule medical apparatus inside the subject is magnetically guided by the effect of the external magnetic field, it is not limited thereto. Specifically, a driving unit that contributes to movement of the capsule medical apparatus can be configured with a self-propelling unit such as a tire and a caterpillar, and an actuator, to arrange the capsule medical apparatus to move by itself using this driving unit. In this case, the external control unit can control the traveling distance and the traveling direction of the capsule medical apparatus that moves by itself by a control signal that is transmitted to the capsule medical apparatus inside the subject.

Moreover, while in the first and the second embodiments, the capsule medical apparatus is fixed on the organ internal wall by a magnetic force (specifically, magnetic attraction or magnetic repulsion) of the external magnetic field, it is not limited thereto. Specifically, a clipping mechanism or the like to fix (detain) the capsule medical apparatus on the organ internal wall can be provided in the capsule medical apparatus, and the capsule medical apparatus can be fixed on the organ internal wall thereby.

Furthermore, while in the first and the second embodiments, the position control unit 10a controls the external magnetic field formed by the magnetically guiding unit 5 so as to match the positions of the living tissue being the treatment target that is selected from the in-vivo image P and the treating unit, it is not limited thereto. Specifically, the movement of the capsule medical apparatus can be controlled manually by operation of the operating unit 7 or the input unit 8 by a user. In this case, to facilitate the manual operation of the movement of the capsule medical apparatus, grid lines can be displayed on the in-vivo image P displayed on the display unit 4. This can be similarly applied to the case where the capsule medical apparatus is arranged to move by itself.

Moreover, while in the first and the second embodiments, the magnetic guidance of the capsule medical apparatus is automatically controlled based on a control of the control unit at the time of bringing the capsule casing into contact with the organ internal wall, it is not limited thereto. Specifically, the movement of the capsule medical apparatus can be manually operated by operation of the operating unit 7 or the input unit 8 by a user. In this case, to facilitate the manual operation of the movement of the capsule medical apparatus, grid lines can be displayed on the in-vivo image P displayed on the display unit 4. This can be similarly applied to the case where the capsule medical apparatus is arranged to move by itself.

Furthermore, while in the first and the second embodiments, a treatment target is selected by input operation of the input unit 8 by a user, it is not limited thereto. Specifically, by performing, in the capsule medical apparatus or in the control unit placed outside a body, a predetermined operation processing and the like on internal information of the subject such as the in-vivo image obtained by capsule medical apparatus, a treatment target can be selected automatically.

If the capsule medical apparatus 2 is not floating in liquid or the like inside the subject, and is always in contact with the organ internal wall, the magnetic guidance or the movement by itself of the capsule medical apparatus to bring the capsule casing into contact with the organ internal wall is not necessary. Moreover, it can be configured to switch between a mode in which the movement of the capsule medical apparatus toward the organ internal wall is controlled and a mode in which the movement of the capsule medical apparatus toward the organ internal wall is not automatically controlled, corresponding to an organ having a relatively large internal space such as a stomach and a large intestine and an organ having a relatively small internal space such as a small intestine.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A capsule medical system comprising:
  a capsule medical apparatus that is introduced into a subject, and includes an imaging unit for taking an in-vivo image of the subject, a treating unit for treating a living tissue inside the subject, and a driving unit for contributing to movement of the capsule medical apparatus;
  a selecting unit that selects a treatment target of the treating unit from the in-vivo image;

a control unit that determines a relative distance between the treatment target and the treating unit, and that moves the capsule medical apparatus in an imaging direction of the imaging unit by a distance corresponding to the relative distance using the driving unit;

a communicating unit that is arranged inside the capsule medical apparatus and that transmits at least the in-vivo image to an external device;

an external communicating unit that receives the in-vivo image transmitted by the communicating unit; and a display unit that displays the in-vivo image received by the external communicating unit, wherein the selecting unit selects the treatment target of the treating unit from the in-vivo image displayed by the display unit;

the imaging unit is arranged at a fixed position relative to the treating unit, the driving unit moves the capsule medical apparatus to a specific position inside the subject at which the in-vivo image showing the treatment target at an image edge portion can be taken by the imaging unit, and the control unit determines the relative distance that is a sum of a specific distance between the treatment target and the imaging unit and an inter-parts distance between the imaging unit and the treating unit, when the capsule medical apparatus stops at the specific position inside the subject in contact with an organ internal wall, the specific distance being defined by an angle of view of the imaging unit.

2. The capsule medical system according to claim 1, wherein the capsule medical apparatus includes a gravity sensor that detects an angle formed between a direction of the treating unit and a direction of gravity, the communicating unit transmits a detection angle detected by the gravity sensor to the external communicating unit, and the control unit obtains the detection angle detected by the gravity sensor through the external communicating unit, and causes the display unit to display the in-vivo image in such a manner that an axial direction of a rectangular coordinate system of the display unit and a direction of the in-vivo image corresponding to a direction of the treating unit are matched with each other, based on the detection angle.

3. The capsule medical system according to claim 2, wherein the selecting unit is an input unit that inputs position coordinate information of the treatment target in the rectangular coordinate system of the display unit, and the control unit calculates a rotation angle formed between the direction of the treating unit and a direction of the treatment target based on the axial direction of the rectangular coordinate system of the display unit and the position coordinate information of the treatment target, and rotates the capsule medical apparatus by the rotation angle using the driving unit.

4. The capsule medical system according to claim 1, wherein the driving unit brings capsule medical apparatus into contact with an organ internal wall near the treatment target by moving the capsule medical apparatus.

5. The capsule medical system according to claim 1, further comprising a magnetically guiding unit that applies an external magnetic field to the capsule medical apparatus that is introduced inside the subject, and that guides the capsule medical apparatus by an effect of the external magnetic field, wherein the driving unit is a magnet that moves or rotates the capsule medical apparatus by the effect of the external magnetic field that is formed by the magnetically guiding unit.

6. The capsule medical system according to claim 5, wherein the driving unit fixes the capsule medical apparatus on an organ internal wall by the effect of the external magnetic field that is formed by the magnetically guiding unit.

7. The capsule medical system according to claim 1, wherein the driving unit moves and rotates the capsule medical apparatus based on a control of the control unit.

8. The capsule medical system according to claim 7, wherein the capsule medical apparatus includes a fixing unit that fixes the capsule medical apparatus to an organ internal wall.

9. The capsule medical system according to claim 1, wherein the treating unit is any one of an obtaining unit that obtains the treatment target, a medicine injecting unit that injects a medicine into the treatment target, a medicine releasing unit that releases a medicine to the treatment target, and a therapy unit that gives a therapy to the treatment target.

10. A method for treating a desired region inside a subject with a capsule medical system, comprising the steps for:

introducing a capsule medical apparatus into a subject, obtaining in-vivo images of the subject using an imaging unit disposed in the capsule medical apparatus therein, transmitting said in-vivo images to an external device using a communicating unit disposed in the capsule medical apparatus therein, moving the capsule medical apparatus using a driving unit and treating a desired region inside the subject using a treating unit disposed in the capsule medical apparatus therein;

receiving the in-vivo images by an external communicating unit;

displaying the in-vivo images received by the external communicating unit through a display unit;

selecting a treatment target inside the subject by a selecting unit from the in-vivo image displayed;

calculating relative positions of the treatment target selected and the capsule medical apparatus by a control unit and determining the relative distance that is a sum of a specific distance between the treatment target and the imaging unit and an inter-parts distance between the imaging unit and the treating unit, the specific distance being defined by an angle of view of the imaging unit, moving the capsule medical in an imaging direction of the imaging unit by a distance corresponding to the relative distance using the driving unit based on the calculated relative positions;

fixing positions of the treatment target and the imaging unit disposed in the capsule medical apparatus; and treating the treatment target with the capsule medical apparatus.

11. The method according to claim 10, wherein the relative positions are determined by bringing the capsule medical apparatus into contact with an organ internal wall of the subject;

calculating a relative distance between the selected treatment target and a treating unit of the capsule medical apparatus; and calculating a relative angle between the selected treatment target and the treating unit.

* * * * *